United States Patent
Ubasawa et al.

(10) Patent No.: US 6,197,775 B1
(45) Date of Patent: *Mar. 6, 2001

(54) PHOSPHONATE NUCLEOTIDE DERIVATIVES

(75) Inventors: Masaru Ubasawa; Hideaki Takashima; Kouichi Sekiya; Naoko Inoue; Satoshi Yuasa; Naohiro Kamiya, all of Kanagawa (JP)

(73) Assignee: Mitsubishi Chemical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,762
(22) PCT Filed: Jun. 14, 1996
(86) PCT No.: PCT/JP96/01631
  § 371 Date: Dec. 11, 1997
  § 102(e) Date: Dec. 11, 1997
(87) PCT Pub. No.: WO97/00262
  PCT Pub. Date: Jan. 3, 1997

(30) Foreign Application Priority Data

Jun. 15, 1995 (JP) .................................... 7-149014

(51) Int. Cl.[7] ................ A01N 43/90; C07D 473/00
(52) U.S. Cl. ........................................ 514/261; 544/277
(58) Field of Search .............................. 544/277; 514/261

(56) References Cited

FOREIGN PATENT DOCUMENTS

| 632048 | * | 4/1995 | (EP) . |
| 94/03467 | * | 2/1994 | (WO) . |
| WO96/33200 | | 10/1996 | (WO) . |

* cited by examiner

Primary Examiner—Mukund J. Shah
Assistant Examiner—Tamthom N. Truong
(74) Attorney, Agent, or Firm—Wenderoth, Lind & Ponack, L.L.P.

(57) ABSTRACT

A compound represented by the following general formula (I) which has an antiviral activity:

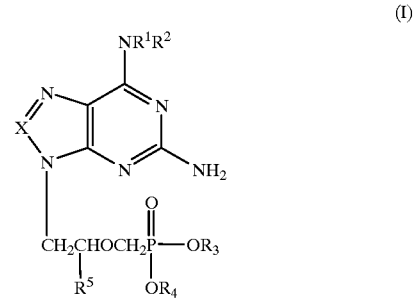

wherein $R^1$ represents hydrogen atom, $C_1$–$C_6$ alkyl group, or $C_7$–$C_{10}$ aralkyl group; $R^2$ represents $C_1$–$C_6$ alkyl group, $C_7$–$C_{10}$ aralkyl group, or phenyl group; $R^3$ and $R^4$ independently represent hydrogen atom, $C_1$–$C_6$ alkyl group, acyloxymethyl group, acylthioethyl group, or ethyl gorup substituted with at least one halogen atom; $R^5$ represents hydrogen atom, $C_1$–$C_4$ alkyl gorup, $C_1$–$C_4$ hydroxyalkyl group, $C_1$–$C_4$ alkyl group substituted with at least one halogen atom; and X represents carbon atom or nitrogen atom.

13 Claims, No Drawings

PHOSPHONATE NUCLEOTIDE DERIVATIVES

This application is a 371 of International Application No. PCT/JP96/01631 filed Jun. 14, 1996.

1. Technical Field

The present invention relates to novel phosphonate nucleotide derivatives. More specifically, it relates to novel phosphonate nucleotide derivatives which have antiviral activity and are useful as active ingredients of medicaments.

2. Background Art

Viral infectious diseases are recognized as a major medical problem, and to achieve therapeutic treatment of these diseases, it has been attempted to develop medicaments having antiviral activity and not exhibiting growth inhibitory activity on healthy cellular systems. For example, a class of phosphonate nucleotides has been intensively studied recently as compounds having selective toxicity against viruses. More specifically, it has been reported that 9-(2-phosphonylmethoxy)ethyladenine (PMEA), 9-(2-phosphonylmethoxy)ethyl-2,6-diaminopurine (PMDAP) and the like are effective against herpes simplex viruses type-1 and type-2 (HSV-1 and HSV-2), human immunodeficiency virus (HIV), and human hepatitis B virus (HBV) (Yokota et al., Antimicrob. Agents Chemother., 35, 394 (1991); and Votruba et al. Mol. Pharmacol., 32, 524 (1987)).

However, these known phosphonate nucleotides may possibly have toxicity to a living body, including myeloid cell growth inhibition as a typical example, and mutagenicity, and their problems have been pointed out from a viewpoint of safety (Antiviral Research, 16, 77 (1991)). In addition, these compounds have insufficient oral absorbability (DeClercq et al., Antimicrob. Agents Chemother., 33, 185 (1989)), and accordingly, parenteral administration such as intravenous injection or intramuscular injection is unavoidably applied in order to obtain an essential blood concentration for exhibiting efficacy. Therapeutic treatment by parenteral administration cannot be applied to patients other than inpatients, and such method is undesired for treatment of diseases such as AIDS or hepatitis B virus infectious disease which require long-term therapy.

On the other hand, the inventors of the present invention found that specific ester derivatives of phosphonate nucleotides have antiviral activity and high oral absorbability (European Patent Publication No. 632,048). Howver, the derivatives have not yet been clinically developed.

DISCLOSURE OF THE INVENTION

The inventors of the present invention conducted intensive researches to solve the foregoing problems, and a result, they found that a specific class of phosphonate nucleotides having novel chemical structures have higher antiviral activity compared to compounds already reported, and that they are safer to a living body and have high oral absorbability. The present invention was achieved on the basis of these findings.

The present invention thus provides phosphonate nucleotide derivatives represented by the following general formula (I) and salts thereof, and hydrates and solvates thereof:

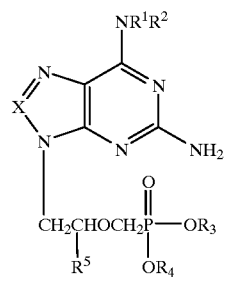

In the above formula, $R^1$ represents hydrogen atom, a $C_1$–$C_6$ alkyl group, or a $C_7$–$C_{10}$ aralkyl group; $R^2$ represents a $C_1$–$C_6$ alkyl group, a $C_7$–$C_{10}$ aralkyl group, or phenyl group, $R^3$ and $R^4$ each independently represent hydrogen atom, a $C_1$–$C_6$ alkyl group, an acyloxymethyl group, an acylthioethyl group, or an ethyl group substituted with one or more halogen atoms; $R^5$ represents hydrogen atom, a $C_1$–$C_4$ alkyl group, a $C_1$–$C_4$ hydroxyalkyl group, or a $C_1$–$C_4$ alkyl group substituted with one or more halogen atoms; and X represents —CH— or nitrogen atom.

According to further embodiments of the present invention, there are provided medicaments comprising the above substances; pharmaceutical compositions and antiviral agents comprising the above substances as an active ingredient. In addition, there are also provided uses of the above substances for the manufacture of pharmaceutical compositions having antiviral activity, and methods for treatment of viral infectious diseases comprising the step of administering a therapeutically effective amount of the above substance to a patient.

BEST MODE FOR CARRYING OUT THE INVENTION

In the phosphonate nucleotide derivatives of the above general formula (I), examples of the $C_1$–$C_6$ alkyl group represented by $R^1$, $R^2$, $R^3$, and $R^4$ include, for example, methyl group, ethyl group, n-propyl group, isopropyl group, n-butyl group, isobutyl group, sec-butyl group, tert-butyl group, n-pentyl group, n-hexyl group or the like.

Examples of the $C_7$–$C_{10}$ aralkyl group represented by $R^1$ and $R^2$ include, for example, benzyl group, phenethyl group, phenylpropyl group, phenylbutyl group or the like.

In particular, hydrogen atom and a $C_1$–$C_4$ alkyl group are preferred as $R^1$, and a $C_1$–$C_4$ alkyl group, benzyl group, and phenyl group are preferred as $R^2$. As $R^2$, a $C_1$–$C_4$ alkyl group and phenyl group are particularly preferred. The $C_1$–$C_4$ alkyl group represented by $R^5$ may be, for example, methyl group, ethyl group, n-propyl group, isopropyl group, n-butyl group, isobutyl group, sec-butyl group, tert-butyl group or the like.

The acyloxymethyl group represented by $R^3$ and $R^4$ may be, for example, acetyloxymethyl group, propionyloxymethyl group, butyryloxymethyl group, isobutyryloxymethyl group, valeryloxymethyl group, isovaleryloxymethyl group, pivaloyloxymethyl group or the like.

The acylthioethyl group represented by $R^3$ and $R^4$ may be, for example, acetylthioethyl group, propionylthioethyl group, butyrylthioethyl group, isobutyrylthioethyl group, valerylthioethyl group, isovalerylthioethyl group, pivaloylthioethyl group or the like.

In the ethyl group substituted with one or more halogen atoms represented by $R^3$ and $R^4$, the halogen atom includes fluorine atom, chlorine atom, bromine atom, and iodine atom. Examples of the ethyl group substituted with one or more halogen atoms include 1-fluoroethyl group, 2-fluoroethyl group, 1-chloroethyl group, 2-chloroethyl group, 2-bromoethyl group, 2,2-difluoroethyl group, 2,2-dichloroethyl group, 2,2-dibromoethyl group, 2,2,2-trifluoroethyl group, 2,2,2-trichloroethyl group, 2,2,2-tribromoethyl group and the like. In particular, ethyl groups substituted at the 2-position are preferred, and fluorine atom is preferred as the halogen atom.

As $R^3$ and $R^4$, a $C_1$–$C_6$ alkyl group or an ethyl group substituted with one or more halogen atoms are preferred, and 2,2,2-trifluoroethyl group is particularly preferred.

Examples of the $C_1$–$C_4$ hydroxyalkyl group represented by $R^5$ include hydroxymethyl group, 1-hydroxyethyl group, 2-hydroxyethyl group, 1-hydroxypropyl group, 2-hydroxypropyl group, 3-hydroxypropyl group, 1-hydroxybutyl group, 2-hydroxybutyl group, 3-hydroxybutyl group, 4-hydroxybutyl group and the like.

In the $C_1$–$C_4$ alkyl group substituted with one or more halogen atoms represented by $R^5$, examples of the halogen atom include fluorine atom and chlorine atoms or the like, and examples of the $C_1$–$C_4$ alkyl group include methyl group, ethyl group, n-propyl group, isopropyl group, n-butyl group, isobutyl group, sec-butyl group, tert-butyl group or the like. Examples of the $C_1$–$C_4$ alkyl group substituted with one or more halogen atoms include fluoromethyl group, difluoromethyl group, trifluoromethyl group, fluoroethyl group, chloroethyl group, fluoropropyl group, chloropropyl group, fluorobutyl group, chlorobutyl group and the like.

Hydrogen atom or a $C_1$–$C_4$ alkyl group is preferred as $R^5$.

The compounds of the present invention are characterized in that they have higher antiviral activity compared to a compound disclosed in European Patent Publication No. 632,048, which is derived by the replacement of the amino group at the 6-position of purine ring with a substituted amino group, and that they are safer to living bodies and can achieve higher oral absorbability. Among the compounds of the present invention, its has been found that those having phenyl group as $R^2$ are characterized to have lower toxicity compared to those having an alkyl group or aralkyl group as $R^2$, and those having an alkyl group as $R^5$ are characterized to have lower toxicity compared to those having hydrogen atom, hydroxyalkyl group, or an alkyl group substituted with one or more halogen atoms as $R^5$.

Examples of particularly preferred compounds among the compounds of the present invention include:

2-amino-9-[2-[bis(2,2,2-trifluoroethyl) phosphonylmethoxy]ethyl]-6-(phenylamino)purine;

2-amino-9-[2-[bis(2,2,2-trifluoroethyl) phosphonylmethoxy]ethyl]-6-(N-methylphenylamino) purine;

2-amino-9-[2-[bis(2,2,2-trifluoroethyl) phosphonylmethoxy]propyl]-6-(phenylamino)purine;

2-amino-9-[2-[bis(2,2,2-trifluoroethyl) phosphonylmethoxy]propyl]-6-(N-methylphenylamino)purine; and 2-amino-9-[2-[bis(2,2,2-trifluoroethyl) phosphonylmethoxy]propyl]-6-(dimethylamino) purine.

The phosphonate nucleotide derivatives of the present invention represented by the above general formula (I) may form pharmacologically and pharmaceutically acceptable salts. Specific examples of such salts include, when they have an acidic group, a metal salt such as lithium salt, sodium salt, potassium salt, magnesium salt, and calcium salt, an ammonium salt such as ammonium salt, methylammonium salt, dimethylammonium salt, trimethylammonium salt, and dicyclohexylammonium salt and other. When a basic group exists, they can form mineral acid salts such as hydrochloride, hydrobromide, sulfate, nitrate, and phosphate, or organic acid salts such as methanesulfonate, benzenesulfonate, p-toluenesulfonate, acetate, propionate, tartrate, fumarate, maleate, malate, oxalate, succinate, citrate, benzoate, mandelate, cinnamate, and lactate.

The phosphonate nucleotide derivatives of the present invention represented by the above general formula (I) and salts thereof may exist in the form of a hydrate or a solvate. Examples of solvents which can form the solvate include methanol, ethanol, isopropanol, acetone, ethyl acetate, methylene chloride and the like. It should be understood that the compounds represented by the general formula (I) as a free form and salts thereof, and their hydrates and solvates fall within the scope of the present invention.

Specific examples of the compound of the present invention are shown in Table 1 set out below. In the table, "Me" represents methyl group, "Et" represents ethyl group, "n-Pr" represents n-propyl group, "i-Pr" represents isopropyl group, "n-Bu" represents n-butyl group, "t-Bu" represents tertiary butyl group, and "Ph" represents phenyl group.

TABLE 1

| Compound No. | $R^1$ | $R^2$ | $R^3$ | $R^4$ | $R^5$ | X |
|---|---|---|---|---|---|---|
| 1 | H | Me | $CF_3CH_2$— | $CF_3CH_2$— | H | C |
| 2 | H | Et | $CF_3CH_2$— | $CF_3CH_2$— | H | C |
| 3 | H | n-Pr | $CF_3CH_2$— | $CF_3CH_2$— | H | C |
| 4 | H | i-Pr | $CF_3CH_2$— | $CF_3CH_2$— | H | C |
| 5 | H | n-Bu | $CF_3CH_2$— | $CF_3CH_2$— | H | C |
| 6 | H | Me | $CF_3CH_2$— | $CF_3CH_2$— | H | N |
| 7 | H | Et- | $CF_3CH_2$— | $CF_3CH_2$— | H | N |
| 8 | H | n-Pr | $CF_3CH_2$— | $CF_3CH_2$— | H | N |
| 9 | H | i-Pr | $CF_3CH_2$— | $CF_3CH_2$— | H | N |
| 10 | H | n-Bu | $CF_3CH_2$— | $CF_3CH_2$— | H | N |
| 11 | Me | Me | $CF_3CH_2$— | $CF_3CH_2$— | H | C |
| 12 | Me | Et | $CF_3CH_2$— | $CF_3CH_2$— | H | C |
| 13 | Me | n-Pr | $CF_3CH_2$— | $CF_3CH_2$— | H | C |
| 14 | Me | i-Pr | $CF_3CH_2$— | $CF_3CH_2$— | H | C |
| 15 | Me | n-Bu | $CF_3CH_2$— | $CF_3CH_2$— | H | C |
| 16 | Et | Et | $CF_3CH_2$— | $CF_3CH_2$— | H | C |

TABLE 1-continued

| Compound No. | R¹ | R² | R³ | R⁴ | R⁵ | X |
|---|---|---|---|---|---|---|
| 17 | Et | n-Pr | CF₃CH₂— | CF₃CH₂— | H | C |
| 18 | Et | i-Pr | CF₃CH₂— | CF₃CH₂— | H | C |
| 19 | Et | n-Bu | CF₃CH₂— | CF₃CH₂— | H | C |
| 20 | n-Pr | n-Pr | CF₃CH₂— | CF₃CH₂— | H | C |
| 21 | Me | Me | CF₃CH₂— | CF₃CH₂— | H | N |
| 22 | Me | Et | CF₃CH₂— | CF₃CH₂— | H | N |
| 23 | Me | n-Pr | CF₃CH₂— | CF₃CH₂— | H | N |
| 24 | Me | i-Pr | CF₃CH₂— | CF₃CH₂— | H | N |
| 25 | Me | n-Bu | CF₃CH₂— | CF₃CH₂— | H | N |
| 26 | Et | Et | CF₃CH₂— | CF₃CH₂— | H | N |
| 27 | Et | n-Pr | CF₃CH₂— | CF₃CH₂— | H | N |
| 28 | Et | i-Pr | CF₃CH₂— | CF₃CH₂— | H | N |
| 29 | Et | n-Bu | CF₃CH₂— | CF₃CH₂— | H | N |
| 30 | n-Pr | n-Pr | CF₃CH₂— | CF₃CH₂— | H | N |
| 31 | H | Me | Me | CF₃CH₂— | H | C |
| 32 | H | Et | Me | CF₃CH₂— | H | C |
| 33 | H | n-Pr | Me | CF₃CH₂— | H | C |
| 34 | H | i-Pr | Me | CF₃CH₂— | H | C |
| 35 | H | n-Bu | Me | CF₃CH₂— | H | C |
| 36 | H | Me | Me | CF₃CH₂— | H | N |
| 37 | H | Et | Me | CF₃CH₂— | H | N |
| 38 | H | n-Pr | Me | CF₃CH₂— | H | N |
| 39 | H | i-Pr | Me | CF₃CH₂— | H | N |
| 40 | H | n-Bu | Me | CF₃CH₂— | H | N |
| 41 | Me | Me | Me | CF₃CH₂— | H | C |
| 42 | Me | Et | Me | CF₃CH₂— | H | C |
| 43 | Me | n-Pr | Me | CF₃CH₂— | H | C |
| 44 | Me | i-Pr | Me | CF₃CH₂— | H | C |
| 45 | Me | n-Bu | Me | CF₃CH₂— | H | C |
| 46 | Et | Et | Me | CF₃CH₂— | H | C |
| 47 | Et | n-Pr | Me | CF₃CH₂— | H | C |
| 48 | Et | i-Pr | Me | CF₃CH₂— | H | C |
| 49 | Et | n-Bu | Me | CF₃CH₂— | H | C |
| 50 | n-Pr | n-Pr | Me | CF₃CH₂— | H | C |
| 51 | Me | Me | Me | CF₃CH₂— | H | N |
| 52 | Me | Et | Me | CF₃CH₂— | H | N |
| 53 | Me | n-Pr | Me | CF₃CH₂— | H | N |
| 54 | Me | i-Pr | Me | CF₃CH₂— | H | N |
| 55 | Me | n-Bu | Me | CF₃CH₂— | H | N |
| 56 | Et | Et | Me | CF₃CH₂— | H | N |
| 57 | Et | n-Pr | Me | CF₃CH₂— | H | N |
| 58 | Et | i-Pr | Me | CF₃CH₂— | H | N |
| 59 | Et | n-Bu | Me | CF₃CH₂— | H | N |
| 60 | n-Pr | n-Pr | Me | CF₃CH₂— | H | N |
| 61 | H | Me | CF₃CH₂— | H | H | C |
| 62 | H | Et | CF₃CH₂— | H | H | C |
| 63 | H | n-Pr | CF₃CH₂— | H | H | C |
| 64 | H | i-Pr | CF₃CH₂— | H | H | C |
| 65 | H | n-Bu | CF₃CH₂— | H | H | C |
| 66 | H | Me | CF₃CH₂— | H | H | N |
| 67 | H | Et | CF₃CH₂— | H | H | N |
| 68 | H | n-Pr | CF₃CH₂— | H | H | N |
| 69 | H | i-Pr | CF₃CH₂— | H | H | N |
| 70 | H | n-Bu | CF₃CH₂— | H | H | N |
| 71 | Me | Me | CF₃CH₂— | H | H | C |
| 72 | Me | Et | CF₃CH₂— | H | H | C |
| 73 | Me | n-Pr | CF₃CH₂— | H | H | C |
| 74 | Me | i-Pr | CF₃CH₂— | H | H | C |
| 75 | Me | n-Bu | CF₃CH₂— | H | H | C |
| 76 | Et | Et | CF₃CH₂— | H | H | C |
| 77 | Et | n-Pr | CF₃CH₂— | H | H | C |
| 78 | Et | i-Pr | CF₃CH₂— | H | H | C |
| 79 | Et | n-Bu | CF₃CH₂— | H | H | C |
| 80 | n-Pr | n-Pr | CF₃CH₂— | H | H | C |
| 81 | Me | Me | CF₃CH₂— | H | H | N |
| 82 | Me | Et | CF₃CH₂— | H | H | N |
| 83 | Me | n-Pr | CF₃CH₂— | H | H | N |
| 84 | Me | i-Pr | CF₃CH₂— | H | H | N |
| 85 | Me | n-Bu | CF₃CH₂— | H | H | N |
| 86 | Et | Et | CF₃CH₂— | H | H | N |
| 87 | Et | n-Pr | CF₃CH₂— | H | H | N |
| 88 | Et | i-Pr | CF₃CH₂— | H | H | N |
| 89 | Et | n-Bu | CF₃CH₂— | H | H | N |
| 90 | n-Pr | n-Pr | CF₃CH₂— | H | H | N |
| 91 | H | Me | H | H | H | C |

TABLE 1-continued

| Compound No. | R¹ | R² | R³ | R⁴ | R⁵ | X |
|---|---|---|---|---|---|---|
| 92 | H | Et | H | H | H | C |
| 93 | H | n-Pr | H | H | H | C |
| 94 | H | i-Pr | H | H | H | C |
| 95 | H | n-Bu | H | H | H | C |
| 96 | H | Me | H | H | H | N |
| 97 | H | Et | H | H | H | N |
| 98 | H | n-Pr | H | H | H | N |
| 99 | H | i-Pr | H | w | H | N |
| 100 | H | n-Bu | H | H | H | N |
| 101 | Me | Me | H | H | H | C |
| 102 | Me | Et | H | H | H | C |
| 103 | Me | n-Pr | H | H | H | C |
| 104 | Me | i-Pr | H | H | H | C |
| 105 | Me | n-Bu | H | H | H | C |
| 106 | Et | Et | H | H | H | C |
| 107 | Et | n-Pr | H | H | H | C |
| 108 | Et | i-Pr | H | H | H | C |
| 109 | Et | n-Bu | H | H | H | C |
| 110 | n-Pr | n-Pr | H | H | H | C |
| 111 | Me | Me | H | H | H | N |
| 112 | Me | Et | H | H | H | N |
| 113 | Me | n-Pr | H | H | H | N |
| 114 | Me | i-Pr | H | H | H | N |
| 115 | Me | n-Bu | H | H | H | N |
| 116 | Et | Et | H | H | H | N |
| 117 | Et | n-Pr | H | H | H | N |
| 118 | Et | i-Pr | H | H | H | N |
| 119 | Et | n-Bu | H | H | H | N |
| 120 | n-Pr | n-Pr | H | H | H | N |
| 121 | H | —CH$_2$-Ph | CF$_3$CH$_2$— | CF$_3$CH$_2$— | H | C |
| 122 | H | —CH$_2$-Ph | H | CF$_3$CH$_2$— | H | C |
| 123 | H | —CH$_2$-Ph | Me | CF$_3$CH$_2$— | H | C |
| 124 | H | —CH$_2$-Ph | H | H | H | C |
| 125 | H | —CH$_2$-Ph | CF$_3$CH$_2$— | CF$_3$CH$_2$— | H | N |
| 126 | H | —CH$_2$-Ph | Me | CF$_3$CH$_2$— | H | N |
| 127 | H | —CH$_2$-Ph | H | CF$_3$CH$_2$— | H | N |
| 128 | H | —CH$_2$-Ph | H | H | H | N |
| 129 | Me | —CH$_2$-Ph | CF$_3$CH$_2$— | CF$_3$CH$_2$— | H | C |
| 130 | Me | —CH$_2$-Ph | Me | CF$_3$CH$_2$— | H | C |
| 131 | Me | —CH$_2$-Ph | H | CF$_3$CH$_2$— | H | C |
| 132 | Me | —CH$_2$-Ph | H | H | H | C |
| 133 | Me | —CH$_2$-Ph | CF$_3$CH$_2$— | CF$_3$CH$_2$— | H | N |
| 134 | Me | —CH$_2$-Ph | Me | CF$_3$CH$_2$— | H | N |
| 135 | Me | —CH$_2$-Ph | H | CF$_3$CH$_2$— | H | N |
| 136 | Me | —CH$_2$-Ph | H | H | H | N |
| 137 | H | Me | CF$_3$CH$_2$— | CF$_3$CH$_2$— | —CH$_2$F | C |
| 138 | H | Et | CF$_3$CH$_2$— | CF$_3$CH$_2$— | —CH$_2$F | C |
| 139 | H | n-Pr | CF$_3$CH$_2$— | CF$_3$CH$_2$— | —CH$_2$F | C |
| 140 | H | i-Pr | CF$_3$CH$_2$— | CF$_3$CH$_2$— | —CH$_2$F | C |
| 141 | H | n-Bu | CF$_3$CH$_2$— | CF$_3$CH$_2$— | —CH$_2$F | C |
| 142 | H | Me | CF$_3$CH$_2$— | CF$_3$CH$_2$— | —CH$_2$F | N |
| 143 | H | Et | CF$_3$CH$_2$— | CF$_3$CH$_2$— | —CH$_2$F | N |
| 144 | H | n-Pr | CF$_3$CH$_2$— | CF$_3$CH$_2$— | —CH$_2$F | N |
| 145 | H | i-Pr | CF$_3$CH$_2$— | CF$_3$CH$_2$— | —CH$_2$F | N |
| 146 | H | n-Bu | CF$_3$CH$_2$— | CF$_3$CH$_2$— | —CH$_2$F | N |
| 147 | Me | Me | CF$_3$CH$_2$— | CF$_3$CH$_2$— | —CH$_2$F | C |
| 148 | Me | Et | CF$_3$CH$_2$— | CF$_3$CH$_2$— | —CH$_2$F | C |
| 149 | Me | n-Pr | CF$_3$CH$_2$— | CF$_3$CH$_2$— | —CH$_2$F | C |
| 150 | Me | i-Pr | CF$_3$CH$_2$— | CF$_3$CH$_2$— | —CH$_2$F | C |
| 151 | Me | n-Bu | CF$_3$CH$_2$— | CF$_3$CH$_2$— | —CH$_2$F | C |
| 152 | Et | Et | CF$_3$CH$_2$— | CF$_3$CH$_2$— | —CH$_2$F | C |
| 153 | Et | n-Pr | CF$_3$CH$_2$— | CF$_3$CH$_2$— | —CH$_2$F | C |
| 154 | Et | i-Pr | CF$_3$CH$_2$— | CF$_3$CH$_2$— | —CH$_2$F | C |
| 155 | Et | n-Bu | CF$_3$CH$_2$— | CF$_3$CH$_2$— | —CH$_2$F | C |
| 156 | n-Pr | n-Pr | CF$_3$CH$_2$— | CF$_3$CH$_2$— | —CH$_2$F | C |
| 157 | Me | Me | CF$_3$CH$_2$— | CF$_3$CH$_2$— | —CH$_2$F | N |
| 158 | Me | Et | CF$_3$CH$_2$— | CF$_3$CH$_2$— | —CH$_2$F | N |
| 159 | Me | n-Pr | CF$_3$CH$_2$— | CF$_3$CH$_2$— | —CH$_2$F | N |
| 160 | Me | i-Pr | CF$_3$CH$_2$— | CF$_3$CH$_2$— | —CH$_2$F | N |
| 161 | Me | n-Bu | CF$_3$CH$_2$— | CF$_3$CH$_2$— | —CH$_2$F | N |
| 162 | Et | Et | CF$_3$CH$_2$— | CF$_3$CH$_2$— | —CH$_2$F | N |
| 163 | Et | n-Pr | CF$_3$CH$_2$— | CF$_3$CH$_2$— | —CH$_2$F | N |
| 164 | Et | i-Pr | CF$_3$CH$_2$— | CF$_3$CH$_2$— | CH2F | N |
| 165 | Et | n-Bu | CF$_3$CH$_2$— | CF$_3$CH$_2$— | —CH$_2$F | N |
| 166 | n-Pr | n-Pr | CF$_3$CH$_2$— | CF$_3$CH$_2$— | —CH$_2$F | N |

TABLE 1-continued

| Compound No. | $R^1$ | $R^2$ | $R^3$ | $R^4$ | $R^5$ | X |
|---|---|---|---|---|---|---|
| 167 | H | Me | Me | $CF_3CH_2$— | —$CH_2F$ | C |
| 168 | H | Et | Me | $CF_3CH_2$— | —$CH_2F$ | C |
| 169 | H | n-Pr | Me | $CF_3CH_2$— | —$CH_2F$ | C |
| 170 | H | i-Pr | Me | $CF_3CH_2$— | —$CH_2F$ | C |
| 171 | H | n-Bu | Me | $CF_3CH_2$— | —$CH_2F$ | C |
| 172 | H | Me | Me | $CF_3CH_2$— | —$CH_2F$ | N |
| 173 | H | Et | Me | $CF_3CH_2$— | —$CH_2F$ | N |
| 174 | H | n-Pr | Me | $CF_3CH_2$— | —$CH_2F$ | N |
| 175 | H | i-Pr | Me | $CF_3CH_2$— | —$CH_2F$ | N |
| 176 | H | n-Bu | Me | $CF_3CH_2$— | —$CH_2F$ | N |
| 177 | Me | Me | Me | $CF_3CH_2$— | —$CH_2F$ | C |
| 178 | Me | Et | Me | $CF_3CH_2$— | —$CH_2F$ | C |
| 179 | Me | n-Pr | Me | $CF_3CH_2$— | —$CH_2F$ | C |
| 180 | Me | i-Pr | Me | $CF_3CH_2$— | —$CH_2F$ | C |
| 181 | Me | n-Bu | Me | $CF_3CH_2$— | —$CH_2F$ | C |
| 182 | Et | Et | Me | $CF_3CH_2$— | —$CH_2F$ | C |
| 183 | Et | n-Pr | Me | $CF_3CH_2$— | —$CH_2F$ | C |
| 184 | Et | i-Pr | Me | $CF_3CH_2$— | —$CH_2F$ | C |
| 185 | Et | n-Bu | Me | $CF_3CH_2$— | —$CH_2F$ | C |
| 186 | n-Pr | n-Pr | Me | $CF_3CH_2$— | —$CH_2F$ | C |
| 187 | Me | Me | Me | $CF_3CH_2$— | —$CH_2F$ | N |
| 188 | Me | Et | Me | $CF_3CH_2$— | —$CH_2F$ | N |
| 189 | Me | n-Pr | Me | $CF_3CH_2$— | —$CH_2F$ | N |
| 190 | Me | i-Pr | Me | $CF_3CH_2$— | —$CH_2F$ | N |
| 191 | Me | n-Bu | Me | $CF_3CH_2$— | —$CH_2F$ | N |
| 192 | Et | Et | Me | $CF_3CH_2$— | —$CH_2F$ | N |
| 193 | Et | n-Pr | Me | $CF_3CH_2$— | —$CH_2F$ | N |
| 194 | Et | i-Pr | Me | $CF_3CH_2$— | —$CH_2F$ | N |
| 195 | Et | n-Bu | Me | $CF_3CH_2$— | —$CH_2F$ | N |
| 196 | n-Pr | n-Pr | Me | $CF_3CH_2$— | —$CH_2F$ | N |
| 197 | H | Me | $CF_3CH_2$— | H | —$CH_2F$ | C |
| 198 | H | Et | $CF_3CH_2$— | H | —$CH_2F$ | C |
| 199 | H | n-Pr | $CF_3CH_2$— | H | —$CH_2F$ | C |
| 200 | H | i-Pr | $CF_3CH_2$— | H | —$CH_2F$ | C |
| 201 | H | n-Bu | $CF_3CH_2$— | H | —$CH_2F$ | C |
| 202 | H | Me | $CF_3CH_2$— | H | —$CH_2F$ | N |
| 203 | H | Et | $CF_3CH_2$— | H | —$CH_2F$ | N |
| 204 | H | n-Pr | $CF_3CH_2$— | H | —$CH_2F$ | N |
| 205 | H | i-Pr | $CF_3CH_2$— | H | —$CH_2F$ | N |
| 206 | H | n-Bu | $CF_3CH_2$— | H | —$CH_2F$ | N |
| 207 | Me | Me | $CF_3CH_2$— | H | —$CH_2F$ | C |
| 208 | Me | Et | $CF_3CH_2$— | H | —$CH_2F$ | C |
| 209 | Me | n-Pr | $CF_3CH_2$— | H | —$CH_2F$ | C |
| 210 | Me | i-Pr | $CF_3CH_2$— | H | —$CH_2F$ | C |
| 211 | Me | n-Bu | $CF_3CH_2$— | H | —$CH_2F$ | C |
| 212 | Et | Et | $CF_3CH_2$— | H | —$CH_2F$ | C |
| 213 | Et | n-Pr | $CF_3CH_2$— | H | —$CH_2F$ | C |
| 214 | Et | i-Pr | $CF_3CH_2$— | H | —$CH_2F$ | C |
| 215 | Et | n-Bu | $CF_3CH_2$— | H | —$CH_2F$ | C |
| 216 | n-Pr | n-Pr | $CF_3CH_2$— | H | —$CH_2F$ | C |
| 217 | Me | Me | $CF_3CH_2$— | H | —$CH_2F$ | N |
| 218 | Me | Et | $CF_3CH_2$— | H | —$CH_2F$ | N |
| 219 | Me | n-Pr | $CF_3CH_2$— | H | —$CH_2F$ | N |
| 220 | Me | i-Pr | $CF_3CH_2$— | H | —$CH_2F$ | N |
| 221 | Me | n-Bu | $CF_3CH_2$— | H | —$CH_2F$ | N |
| 222 | Et | Et | $CF_3CH_2$— | H | —$CH_2F$ | N |
| 223 | Et | n-Pr | $CF_3CH_2$— | H | —$CH_2F$ | N |
| 224 | Et | i-Pr | $CF_3CH_2$— | H | —$CH_2F$ | N |
| 225 | Et | n-Bu | $CF_3CH_2$— | H | —$CH_2F$ | N |
| 226 | n-Pr | n-Pr | $CF_3CH_2$— | H | —$CH_2F$ | N |
| 227 | H | Me | H | H | —$CH_2F$ | C |
| 228 | H | Et | H | H | —$CH_2F$ | C |
| 229 | H | n-Pr | H | H | —$CH_2F$ | C |
| 230 | H | i-Pr | H | H | —$CH_2F$ | C |
| 231 | H | n-Bu | H | H | —$CH_2F$ | C |
| 232 | H | Me | H | H | —$CH_2F$ | N |
| 233 | H | Et | H | H | —$CH_2F$ | N |
| 234 | H | n-Pr | H | H | —$CH_2F$ | N |
| 235 | H | i-Pr | H | H | —$CH_2F$ | N |
| 236 | H | n-Bu | H | H | —$CH_2F$ | N |
| 237 | Me | Me | H | H | —$CH_2F$ | C |
| 238 | Me | Et | H | H | —$CH_2F$ | C |
| 239 | Me | n-Pr | H | H | —$CH_2F$ | C |
| 240 | Me | i-Pr | H | H | —$CH_2F$ | C |
| 241 | Me | n-Bu | H | H | —$CH_2F$ | C |

TABLE 1-continued

| Compound No. | R¹ | R² | R³ | R⁴ | R⁵ | X |
|---|---|---|---|---|---|---|
| 242 | Et | Et | H | H | —CH$_2$F | C |
| 243 | Et | n-Pr | H | H | —CH$_2$F | C |
| 244 | Et | i-Pr | H | H | —CH$_2$F | C |
| 245 | Et | n-Bu | H | H | —CH$_2$F | C |
| 246 | n-Pr | n-Pr | H | H | —CH$_2$F | C |
| 247 | Me | Me | H | H | —CH$_2$F | N |
| 248 | Me | Et | H | H | —CH$_2$F | N |
| 249 | Me | n-Pr | H | H | —CH$_2$F | N |
| 250 | Me | i-Pr | H | H | —CH$_2$F | N |
| 251 | Me | n-Bu | H | H | —CH$_2$F | N |
| 252 | Et | Et | H | H | —CH$_2$F | N |
| 253 | Et | n-Pr | H | H | —CH$_2$F | N |
| 254 | Et | i-Pr | H | H | —CH$_2$F | N |
| 255 | Et | n-Bu | H | H | —CH$_2$F | N |
| 256 | n-Pr | n-Pr | H | H | —CH$_2$F | N |
| 257 | H | Ph | CF$_3$CH$_2$— | CF$_3$CH$_2$— | —CH$_2$F | C |
| 258 | H | Ph | H | CF$_3$CH$_2$— | —CH$_2$F | C |
| 259 | H | Ph | Me | CF$_3$CH$_2$— | —CH$_2$F | C |
| 260 | H | Ph | H | H | —CH$_2$F | C |
| 261 | H | Ph | CF$_3$CH$_2$— | CF$_3$CH$_2$— | —CH$_2$F | N |
| 262 | H | Ph | Me | CF$_3$CH$_2$— | —CH$_2$F | N |
| 263 | H | Ph | H | CF$_3$CH$_2$— | —CH$_2$F | N |
| 264 | H | Ph | H | H | —CH$_2$F | N |
| 265 | Me | Ph | CF$_3$CH$_2$— | CF$_3$CH$_2$— | —CH$_2$F | C |
| 266 | Me | Ph | Me | CF$_3$CH$_2$— | —CH$_2$F | C |
| 267 | Me | Ph | H | CF$_3$CH$_2$— | —CH$_2$F | C |
| 268 | Me | Ph | H | H | —CH$_2$F | C |
| 269 | Me | Ph | CF$_3$CH$_2$— | CF$_3$CH$_2$— | —CH$_2$F | N |
| 270 | Me | Ph | Me | CF$_3$CH$_2$— | —CH$_2$F | N |
| 271 | Me | Ph | H | CF$_3$CH$_2$— | —CH$_2$F | N |
| 272 | Me | Ph | H | H | —CH$_2$F | N |
| 273 | H | Me | CF$_3$CH$_2$— | CF$_3$CH$_2$— | —CH$_2$OH | C |
| 274 | H | Et | CF$_3$CH$_2$— | CF$_3$CH$_2$— | —CH$_2$OH | C |
| 275 | H | n-Pr | CF$_3$CH$_2$— | CF$_3$CH$_2$— | —CH$_2$OH | C |
| 276 | H | i-Pr | CF$_3$CH$_2$— | CF$_3$CH$_2$— | —CH$_2$OH | C |
| 277 | H | n-Bu | CF$_3$CH$_2$— | CF$_3$CH$_2$— | —CH$_2$OH | C |
| 278 | H | Me | CF$_3$CH$_2$— | CF$_3$CH$_2$— | —CH$_2$OH | N |
| 279 | H | Et | CF$_3$CH$_2$— | CF$_3$CH$_2$— | —CH$_2$OH | N |
| 280 | H | n-Pr | CF$_3$CH$_2$— | CF$_3$CH$_2$— | —CH$_2$OH | N |
| 281 | H | i-Pr | CF$_3$CH$_2$— | CF$_3$CH$_2$— | —CH$_2$OH | N |
| 282 | H | n-Bu | CF$_3$CH$_2$— | CF$_3$CH$_2$— | —CH$_2$OH | N |
| 283 | Me | Me | CF$_3$CH$_2$— | CF$_3$CH$_2$— | —CH$_2$OH | C |
| 284 | Me | Et | CF$_3$CH$_2$— | CF$_3$CH$_2$— | —CH$_2$OH | C |
| 285 | Me | n-Pr | CF$_3$CH$_2$— | CF$_3$CH$_2$— | —CH$_2$OH | C |
| 286 | Me | i-Pr | CF$_3$CH$_2$— | CF$_3$CH$_2$— | —CH$_2$OH | C |
| 287 | Me | n-Bu | CF$_3$CH$_2$— | CF$_3$CH$_2$— | —CH$_2$OH | C |
| 288 | Et | Et | CF$_3$CH$_2$— | CF$_3$CH$_2$— | —CH$_2$OH | C |
| 289 | Et | n-Pr | CF$_3$CH$_2$— | CF$_3$CH$_2$— | —CH$_2$OH | C |
| 290 | Et | i-Pr | CF$_3$CH$_2$— | CF$_3$CH$_2$— | —CH$_2$OH | C |
| 291 | Et | n-Bu | CF$_3$CH$_2$— | CF$_3$CH$_2$— | —CH$_2$OH | C |
| 292 | n-Pr | n-Pr | CF$_3$CH$_2$— | CF$_3$CH$_2$— | —CH$_2$OH | C |
| 293 | Me | Me | CF$_3$CH$_2$— | CF$_3$CH$_2$— | —CH$_2$OH | N |
| 294 | Me | Et | CF$_3$CH$_2$— | CF$_3$CH$_2$— | —CH$_2$OH | N |
| 295 | Me | n-Pr | CF$_3$CH$_2$— | CF$_3$CH$_2$— | —CH$_2$OH | N |
| 296 | Me | i-Pr | CF$_3$CH$_2$— | CF$_3$CH$_2$— | —CH$_2$OH | N |
| 297 | Me | n-Bu | CF$_3$CH$_2$— | CF$_3$CH$_2$— | —CH$_2$OH | N |
| 298 | Et | Et | CF$_3$CH$_2$— | CF$_3$CH$_2$— | —CH$_2$OH | N |
| 299 | Et | n-Pr | CF$_3$CH$_2$— | CF$_3$CH$_2$— | —CH$_2$OH | N |
| 300 | Et | i-Pr | CF$_3$CH$_2$— | CF$_3$CH$_2$— | —CH$_2$OH | N |
| 301 | Et | n-Bu | CF$_3$CH$_2$— | CF$_3$CH$_2$— | —CH$_2$OH | N |
| 302 | n-Pr | n-Pr | CF$_3$CH$_2$— | CF$_3$CH$_2$— | —CH$_2$OH | N |
| 303 | H | Me | Me | CF$_3$CH$_2$— | —CH$_2$OH | C |
| 304 | H | Et | Me | CF$_3$CH$_2$— | —CH$_2$OH | C |
| 305 | H | n-Pr | Me | CF$_3$CH$_2$— | —CH$_2$OH | C |
| 306 | H | i-Pr | Me | CF$_3$CH$_2$— | —CH$_2$OH | C |
| 307 | H | n-Bu | Me | CF$_3$CH$_2$— | —CH$_2$OH | C |
| 308 | H | Me | Me | CF$_3$CH$_2$— | —CH$_2$OH | N |
| 309 | H | Et | Me | CF$_3$CH$_2$— | —CH$_2$OH | N |
| 310 | H | n-Pr | Me | CF$_3$CH$_2$— | —CH$_2$OH | N |
| 311 | H | i-Pr | Me | CF$_3$CH$_2$— | —CH$_2$OH | N |
| 312 | H | n-Bu | Me | CF$_3$CH$_2$— | —CH$_2$OH | N |
| 313 | Me | Me | Me | CF$_3$CH$_2$— | —CH$_2$OH | C |
| 314 | Me | Et | Me | CF$_3$CH$_2$— | —CH$_2$OH | C |
| 315 | Me | n-Pr | Me | CF$_3$CH$_2$— | —CH$_2$OH | C |
| 316 | Me | i-Pr | Me | CF$_3$CH$_2$— | —CH$_2$OH | C |

TABLE 1-continued

| Compound No. | R¹ | R² | R³ | R⁴ | R⁵ | X |
|---|---|---|---|---|---|---|
| 317 | Me | n-Bu | Me | CF₃CH₂— | —CH₂OH | C |
| 318 | Et | Et | Me | CF₃CH₂— | —CH₂OH | C |
| 319 | Et | n-Pr | Me | CF₃CH₂— | —CH₂OH | C |
| 320 | Et | i-Pr | Me | CF₃CH₂— | —CH₂OH | C |
| 321 | Et | n-Bu | Me | CF₃CH₂— | —CH₂OH | C |
| 322 | n-Pr | n-Pr | Me | CF₃CH₂— | —CH₂OH | C |
| 323 | Me | Me | Me | CF₃CH₂— | —CH₂OH | N |
| 324 | Me | Et | Me | CF₃CH₂— | —CH₂OH | N |
| 325 | Me | n-Pr | Me | CF₃CH₂— | —CH₂OH | N |
| 326 | Me | i-Pr | Me | CF₃CH₂— | —CH₂OH | N |
| 327 | Me | n-Bu | Me | CF₃CH₂— | —CH₂OH | N |
| 328 | Et | Et | Me | CF₃CH₂— | —CH₂OH | N |
| 329 | Et | n-Pr | Me | CF₃CH₂— | —CH₂OH | N |
| 330 | Et | i-Pr | Me | CF₃CH₂— | —CH₂OH | N |
| 331 | Et | n-Bu | Me | CF₃CH₂— | —CH₂OH | N |
| 332 | n-Pr | n-Pr | Me | CF₃CH₂— | —CH₂OH | N |
| 333 | H | Me | CF₃CH₂— | H | —CH₂OH | C |
| 334 | H | Et | CF₃CH₂— | H | —CH₂OH | C |
| 335 | H | n-Pr | CF₃CH₂— | H | —CH₂OH | C |
| 336 | H | i-Pr | CF₃CH₂— | H | —CH₂OH | C |
| 337 | H | n-Bu | CF₃CH₂— | H | —CH₂OH | C |
| 338 | H | Me | CF₃CH₂— | H | —CH₂OH | N |
| 339 | H | Et | CF₃CH₂— | H | —CH₂OH | N |
| 340 | H | n-Pr | CF₃CH₂— | H | —CH₂OH | N |
| 341 | H | i-Pr | CF₃CH₂— | H | —CH₂OH | N |
| 342 | H | n-Bu | CF₃CH₂— | H | —CH₂OH | N |
| 343 | Me | Me | CF₃CH₂— | H | —CH₂OH | C |
| 344 | Me | Et | CF₃CH₂— | H | —CH₂OH | C |
| 345 | Me | n-Pr | CF₃CH₂— | H | —CH₂OH | C |
| 346 | Me | i-Pr | CF₃CH₂— | H | —CH₂OH | C |
| 347 | Me | n-Bu | CF₃CH₂— | H | —CH₂OH | C |
| 348 | Et | Et | CF₃CH₂— | H | —CH₂OH | C |
| 349 | Et | n-Pr | CF₃CH₂— | H | —CH₂OH | C |
| 350 | Et | i-Pr | CF₃CH₂— | H | —CH₂OH | C |
| 351 | Et | n-Bu | CF₃CH₂— | H | —CH₂OH | C |
| 352 | n-Pr | n-Pr | CF₃CH₂— | H | —CH₂OH | C |
| 353 | Me | Me | CF₃CH₂— | H | —CH₂OH | N |
| 354 | Me | Et | CF₃CH₂— | H | —CH₂OH | N |
| 355 | Me | n-Pr | CF₃CH₂— | H | —CH₂OH | N |
| 356 | Me | i-Pr | CF₃CH₂— | H | —CH₂OH | N |
| 357 | Me | n-Bu | CF₃CH₂— | H | —CH₂OH | N |
| 358 | Et | Et | CF₃CH₂— | H | —CH₂OH | N |
| 359 | Et | n-Pr | CF₃CH₂— | H | —CH₂OH | N |
| 360 | Et | i-Pr | CF₃CH₂— | H | —CH₂OH | N |
| 361 | Et | n-Bu | CF₃CH₂— | H | —CH₂OH | N |
| 362 | n-Pr | n-Pr | CF₃CH₂— | H | —CH₂OH | N |
| 363 | H | Me | H | H | —CH₂OH | C |
| 364 | H | Et | H | H | —CH₂OH | C |
| 365 | H | n-Pr | H | H | —CH₂OH | C |
| 366 | H | i-Pr | H | H | —CH₂OH | C |
| 367 | H | n-Bu | H | H | —CH₂OH | C |
| 368 | H | Me | H | H | —CH₂OH | N |
| 369 | H | Et | H | H | —CH₂OH | N |
| 370 | H | n-Pr | H | H | —CH₂OH | N |
| 371 | H | i-Pr | H | H | —CH₂OH | N |
| 372 | H | n-Bu | H | H | —CH₂OH | N |
| 373 | Me | Me | H | H | —CH₂OH | C |
| 374 | Me | Et | H | H | —CH₂OH | C |
| 375 | Me | n-Pr | H | H | —CH₂OH | C |
| 376 | Me | i-Pr | H | H | —CH₂OH | C |
| 377 | Me | n-Bu | H | H | —CH₂OH | C |
| 378 | Et | Et | H | H | —CH₂OH | C |
| 379 | Et | n-Pr | H | H | —CH₂OH | C |
| 380 | Et | i-Pr | H | H | —CH₂OH | C |
| 381 | Et | n-Bu | H | H | —CH₂OH | C |
| 382 | n-Pr | n-Pr | H | H | —CH₂OH | C |
| 383 | Me | Me | H | H | —CH₂OH | N |
| 384 | Me | Et | H | H | —CH₂OH | N |
| 385 | Me | n-Pr | H | H | —CH₂OH | N |
| 386 | Me | i-Pr | H | H | —CH₂OH | N |
| 387 | Me | n-Bu | H | H | —CH₂OH | N |
| 388 | Et | Et | H | H | —CH₂OH | N |
| 389 | Et | n-Pr | H | H | —CH₂OH | N |
| 390 | Et | i-Pr | H | H | —CH₂OH | N |
| 391 | Et | n-Bu | H | H | —CH₂OH | N |

TABLE 1-continued

| Compound No. | R¹ | R² | R³ | R⁴ | R⁵ | X |
|---|---|---|---|---|---|---|
| 392 | n-Pr | n-Pr | H | H | —CH₂OH | N |
| 393 | H | Ph | CF₃CH₂— | CF₃CH₂— | —CH₂OH | C |
| 394 | H | Ph | H | CF₃CH₂— | —CH₂OH | C |
| 395 | H | Ph | Me | CF₃CH₂— | —CH₂OH | C |
| 396 | H | Ph | H | H | —CH₂OH | C |
| 397 | H | Ph | CF₃CH₂— | CF₃CH₂— | —CH₂OH | N |
| 398 | H | Ph | Me | CF₃CH₂— | —CH₂OH | N |
| 399 | H | Ph | H | CF₃CH₂— | —CH₂OH | N |
| 400 | H | Ph | H | H | —CH₂OH | N |
| 401 | Me | Ph | CF₃CH₂— | CF₃CH₂— | —CH₂OH | C |
| 402 | Me | Ph | Me | CF₃CH₂— | —CH₂OH | C |
| 403 | Me | Ph | H | CF₃CH₂— | —CH₂OH | C |
| 404 | Me | Ph | H | H | —CH₂OH | C |
| 405 | Me | Ph | CF₃CH₂— | CF₃CH₂— | —CH₂OH | N |
| 406 | Me | Ph | Me | CF₃CH₂— | —CH₂OH | N |
| 407 | Me | Ph | H | CF₃CH₂— | —CH₂OH | N |
| 408 | Me | Ph | H | H | —CH₂OH | N |
| 409 | H | Me | —CH₂OCO-t-Bu | —CH₂OCO-t-Bu | Me | C |
| 410 | H | Et | —CH₂OCO-t-Bu | —CH₂OCO-t-Bu | Me | C |
| 411 | H | n-Pr | —CH₂OCO-t-Bu | —CH₂OCO-t-Bu | Me | C |
| 412 | H | i-Pr | —CH₂OCO-t-Bu | —CH₂OCO-t-Bu | Me | C |
| 413 | H | n-Bu | —CH₂OCO-t-Bu | —CH₂OCO-t-Bu | Me | C |
| 414 | H | Me | —CH₂OCO-t-Bu | —CH₂OCO-t-Bu | Me | N |
| 415 | H | Et | —CH₂OCO-t-Bu | —CH₂OCO-t-Bu | Me | N |
| 416 | H | n-Pr | —CH₂OCO-t-Bu | —CH₂OCO-t-Bu | Me | N |
| 417 | H | i-Pr | —CH₂OCO-t-Bu | —CH₂OCO-t-Bu | Me | N |
| 418 | H | n-Bu | —CH₂OCO-t-Bu | —CH₂OCO-t-Bu | Me | N |
| 419 | Me | Me | —CH₂OCO-t-Bu | —CH₂OCO-t-Bu | Me | C |
| 420 | Me | Et | —CH₂OCO-t-Bu | —CH₂OCO-t-Bu | Me | C |
| 421 | Me | n-Pr | —CH₂OCO-t-Bu | —CH₂OCO-t-Bu | Me | C |
| 422 | Me | i-Pr | —CH₂OCO-t-Bu | —CH₂OCO-t-Bu | Me | C |
| 423 | Me | n-Bu | —CH₂OCO-t-Bu | —CH₂OCO-t-Bu | Me | C |
| 424 | Et | Et | —CH₂OCO-t-Bu | —CH₂OCO-t-Bu | Me | C |
| 425 | Et | n-Pr | —CH₂OCO-t-Bu | —CH₂OCO-t-Bu | Me | C |
| 426 | Et | i-Pr | —CH₂OCO-t-Bu | —CH₂OCO-t-Bu | Me | C |
| 427 | Et | n-Bu | —CH₂OCO-t-Bu | —CH₂OCO-t-Bu | Me | C |
| 428 | n-Pr | n-Pr | —CH₂OCO-t-Bu | —CH₂OCO-t-Bu | Me | C |
| 429 | Me | Me | —CH₂OCO-t-Bu | —CH₂OCO-t-Bu | Me | N |
| 430 | Me | Et | —CH₂OCO-t-Bu | —CH₂OCO-t-Bu | Me | N |
| 431 | Me | n-Pr | —CH₂OCO-t-Bu | —CH₂OCO-t-Bu | Me | N |
| 432 | Me | i-Pr | —CH₂OCO-t-Bu | —CH₂OCO-t-Bu | Me | N |
| 433 | Me | n-Bu | —CH₂OCO-t-Bu | —CH₂OCO-t-Bu | Me | N |
| 434 | Et | Et | —CH₂OCO-t-Bu | —CH₂OCO-t-Bu | Me | N |
| 435 | Et | n-Pr | —CH₂OCO-t-Bu | —CH₂OCO-t-Bu | Me | N |
| 436 | Et | i-Pr | —CH₂OCO-t-Bu | —CH₂OCO-t-Bu | Me | N |
| 437 | Et | n-Bu | —CH₂OCO-t-Bu | —CH₂OCO-t-Bu | Me | N |
| 438 | n-Pr | n-Pr | —CH₂OCO-t-Bu | —CH₂OCO-t-Bu | Me | N |
| 439 | H | Me | —CH₂OCO-t-Bu | —CH₂OCO-t-Bu | —CH₂F | C |
| 440 | H | Et | —CH₂OCO-t-Bu | —CH₂OCO-t-Bu | —CH₂F | C |
| 441 | H | n-Pr | —CH₂OCO-t-Bu | —CH₂OCO-t-Bu | —CH₂F | C |
| 442 | H | i-Pr | —CH₂OCO-t-Bu | —CH₂OCO-t-Bu | —CH₂F | C |
| 443 | H | n-Bu | —CH₂OCO-t-Bu | —CH₂OCO-t-Bu | —CH₂F | C |
| 444 | H | Me | —CH₂OCO-t-Bu | —CH₂OCO-t-Bu | —CH₂F | N |
| 445 | H | Et | —CH₂OCO-t-Bu | —CH₂OCO-t-Bu | —CH₂F | N |
| 446 | H | n-Pr | —CH₂OCO-t-Bu | —CH₂OCO-t-Bu | —CH₂F | N |
| 447 | H | i-Pr | —CH₂OCO-t-Bu | —CH₂OCO-t-Bu | —CH₂F | N |
| 448 | H | n-Bu | —CH₂OCO-t-Bu | —CH₂OCO-t-Bu | —CH₂F | N |
| 449 | Me | Me | —CH₂OCO-t-Bu | —CH₂OCO-t-Bu | —CH₂F | C |
| 450 | Me | Et | —CH₂OCO-t-Bu | —CH₂OCO-t-Bu | —CH₂F | C |
| 451 | Me | n-Pr | —CH₂OCO-t-Bu | —CH₂OCO-t-Bu | —CH₂F | C |
| 452 | Me | i-Pr | —CH₂OCO-t-Bu | —CH₂OCO-t-Bu | —CH₂F | C |
| 453 | Me | n-Bu | —CH₂OCO-t-Bu | —CH₂OCO-t-Bu | —CH₂F | C |
| 454 | Et | Et | —CH₂OCO-t-Bu | —CH₂OCO-t-Bu | —CH₂F | C |
| 455 | Et | n-Pr | —CH₂OCO-t-Bu | —CH₂OCO-t-Bu | —CH₂F | C |
| 456 | Et | i-Pr | —CH₂OCO-t-Bu | —CH₂OCO-t-Bu | —CH₂F | C |
| 457 | Et | n-Bu | —CH₂OCO-t-Bu | —CH₂OCO-t-Bu | —CH₂F | C |
| 458 | n-Pr | n-Pr | —CH₂OCO-t-Bu | —CH₂OCO-t-Bu | —CH₂F | C |
| 459 | Me | Me | —CH₂OCO-t-Bu | —CH₂OCO-t-Bu | —CH₂F | N |
| 460 | Me | Et | —CH₂OCO-t-Bu | —CH₂OCO-t-Bu | —CH₂F | N |
| 461 | Me | n-Pr | —CH₂OCO-t-Bu | —CH₂OCO-t-Bu | —CH₂F | N |
| 462 | Me | i-Pr | —CH₂OCO-t-Bu | —CH₂OCO-t-Bu | —CH₂F | N |
| 463 | Me | n-Bu | —CH₂OCO-t-Bu | —CH₂OCO-t-Bu | —CH₂F | N |
| 464 | Et | Et | —CH₂OCO-t-Bu | —CH₂OCO-t-Bu | —CH₂F | N |
| 465 | Et | n-Pr | —CH₂OCO-t-Bu | —CH₂OCO-t-Bu | —CH₂F | N |
| 466 | Et | i-Pr | —CH₂OCO-t-Bu | —CH₂OCO-t-Bu | —CH₂F | N |

TABLE 1-continued

| Compound No. | R¹ | R² | R³ | R⁴ | R⁵ | X |
|---|---|---|---|---|---|---|
| 467 | Et | n-Bu | —CH₂OCO-t-Bu | —CH₂OCO-t-Bu | —CH₂F | N |
| 468 | n-Pr | n-Pr | —CH₂OCO-t-Bu | —CH₂OCO-t-Bu | —CH₂F | N |
| 469 | H | Me | —CH₂OCO-t-Bu | —CH₂OCO-t-Bu | —CH₂OH | C |
| 470 | H | Et | —CH₂OCO-t-Bu | —CH₂OCO-t-Bu | —CH₂OH | C |
| 471 | H | n-Pr | —CH₂OCO-t-Bu | —CH₂OCO-t-Bu | —CH₂OH | C |
| 472 | H | i-Pr | —CH₂OCO-t-Bu | —CH₂OCO-t-Bu | —CH₂OH | C |
| 473 | H | n-Bu | —CH₂OCO-t-Bu | —CH₂OCO-t-Bu | —CH₂OH | C |
| 474 | H | Me | —CH₂OCO-t-Bu | —CH₂OCO-t-Bu | —CH₂OH | N |
| 475 | H | Et | —CH₂OCO-t-Bu | —CH₂OCO-t-Bu | —CH₂OH | N |
| 476 | H | n-Pr | —CH₂OCO-t-Bu | —CH₂OCO-t-Bu | —CH₂OH | N |
| 477 | H | i-Pr | —CH₂OCO-t-Bu | —CH₂OCO-t-Bu | —CH₂OH | N |
| 478 | H | n-Bu | —CH₂OCO-t-Bu | —CH₂OCO-t-Bu | —CH₂OH | N |
| 479 | Me | Me | —CH₂OCO-t-Bu | —CH₂OCO-t-Bu | —CH₂OH | C |
| 480 | Me | Et | —CH₂OCO-t-Bu | —CH₂OCO-t-Bu | —CH₂OH | C |
| 481 | Me | n-Pr | —CH₂OCO-t-Bu | —CH₂OCO-t-Bu | —CH₂OH | C |
| 482 | Me | i-Pr | —CH₂OCO-t-Bu | —CH₂OCO-t-Bu | —CH₂OH | C |
| 483 | Me | n-Bu | —CH₂OCO-t-Bu | —CH₂OCO-t-Bu | —CH₂OH | C |
| 484 | Et | Et | —CH₂OCO-t-Bu | —CH₂OCO-t-Bu | —CH₂OH | C |
| 485 | Et | n-Pr | —CH₂OCO-t-Bu | —CH₂OCO-t-Bu | —CH₂OH | C |
| 486 | Et | i-Pr | —CH₂OCO-t-Bu | —CH₂OCO-t-Bu | —CH₂OH | C |
| 487 | Et | n-Bu | —CH₂OCO-t-Bu | —CH₂OCO-t-Bu | —CH₂OH | C |
| 488 | n-Pr | n-Pr | —CH₂OCO-t-Bu | —CH₂OCO-t-Bu | —CH₂OH | C |
| 489 | Me | Me | —CH₂OCO-t-Bu | —CH₂OCO-t-Bu | —CH₂OH | N |
| 490 | Me | Et | —CH₂OCO-t-Bu | —CH₂OCO-t-Bu | —CH₂OH | N |
| 491 | Me | n-Pr | —CH₂OCO-t-Bu | —CH₂OCO-t-Bu | —CH₂OH | N |
| 492 | Me | i-Pr | —CH₂OCO-t-Bu | —CH₂OCO-t-Bu | —CH₂OH | N |
| 493 | Me | n-Bu | —CH₂OCO-t-Bu | —CH₂OCO-t-Bu | —CH₂OH | N |
| 494 | Et | Et | —CH₂OCO-t-Bu | —CH₂OCO-t-Bu | —CH₂OH | N |
| 495 | Et | n-Pr | —CH₂OCO-t-Bu | —CH₂OCO-t-Bu | —CH₂OH | N |
| 496 | Et | i-Pr | —CH₂OCO-t-Bu | —CH₂OCO-t-Bu | —CH₂OH | N |
| 497 | Et | n-Bu | —CH₂OCO-t-Bu | —CH₂OCO-t-Bu | —CH₂OH | N |
| 498 | n-Pr | n-Pr | —CH₂OCO-t-Bu | —CH₂OCO-t-Bu | —CH₂OH | N |
| 499 | H | Me | —CH₂CH₂S—CO-i-Pr | —CH₂CH₂S—CO-i-Pr | Me | C |
| 500 | H | Et | —CH₂CH₂S—CO-i-Pr | —CH₂CH₂S—CO-i-Pr | Me | C |
| 501 | H | n-Pr | —CH₂CH₂S—CO-i-Pr | —CH₂CH₂S—CO-i-Pr | Me | C |
| 502 | H | i-Pr | —CH₂CH₂S—CO-i-Pr | —CH₂CH₂S—CO-i-Pr | Me | C |
| 503 | H | n-Bu | —CH₂CH₂S—CO-i-Pr | —CH₂CH₂S—CO-i-Pr | Me | C |
| 504 | H | Me | —CH₂CH₂S—CO-i-Pr | —CH₂CH₂S—CO-i-Pr | Me | N |
| 505 | H | Et | —CH₂CH₂S—CO-i-Pr | —CH₂CH₂S—CO-i-Pr | Me | N |
| 506 | H | n-Pr | —CH₂CH₂S—CO-i-Pr | —CH₂CH₂S—CO-i-Pr | Me | N |
| 507 | H | i-Pr | —CH₂CH₂S—CO-i-Pr | —CH₂CH₂S—CO-i-Pr | Me | N |
| 508 | H | n-Bu | —CH₂CH₂S—CO-i-Pr | —CH₂CH₂S—CO-i-Pr | Me | N |
| 509 | Me | Me | —CH₂CH₂S—CO-i-Pr | —CH₂CH₂S—CO-i-Pr | Me | C |
| 510 | Me | Et | —CH₂CH₂S—CO-i-Pr | —CH₂CH₂S—CO-i-Pr | Me | C |
| 511 | Me | n-Pr | —CH₂CH₂S—CO-i-Pr | —CH₂CH₂S—CO-i-Pr | Me | C |
| 512 | Me | i-Pr | —CH₂CH₂S—CO-i-Pr | —CH₂CH₂S—CO-i-Pr | Me | C |
| 513 | Me | n-Bu | —CH₂CH₂S—CO-i-Pr | —CH₂CH₂S—CO-i-Pr | Me | C |
| 514 | Et | Et | —CH₂CH₂S—CO-i-Pr | —CH₂CH₂S—CO-i-Pr | Me | C |
| 515 | Et | n-Pr | —CH₂CH₂S—CO-i-Pr | —CH₂CH₂S—CO-i-Pr | Me | C |
| 516 | Et | i-Pr | —CH₂CH₂S—CO-i-Pr | —CH₂CH₂S—CO-i-Pr | Me | C |
| 517 | Et | n-Bu | —CH₂CH₂S—CO-i-Pr | —CH₂CH₂S—CO-i-Pr | Me | C |
| 518 | n-Pr | n-Pr | —CH₂CH₂S—CO-i-Pr | —CH₂CH₂S—CO-i-Pr | Me | C |
| 519 | Me | Me | —CH₂CH₂S—CO-i-Pr | —CH₂CH₂S—CO-i-Pr | Me | N |
| 520 | Me | Et | —CH₂CH₂S—CO-i-Pr | —CH₂CH₂S—CO-i-Pr | Me | N |
| 521 | Me | n-Pr | —CH₂CH₂S—CO-i-Pr | —CH₂CH₂S—CO-i-Pr | Me | N |
| 522 | Me | i-Pr | —CH₂CH₂S—CO-i-Pr | —CH₂CH₂S—CO-i-Pr | Me | N |
| 523 | Me | n-Bu | —CH₂CH₂S—CO-i-Pr | —CH₂CH₂S—CO-i-Pr | Me | N |
| 524 | Et | Et | —CH₂CH₂S—CO-i-Pr | —CH₂CH₂S—CO-i-Pr | Me | N |
| 525 | Et | n-Pr | —CH₂CH₂S—CO-i-Pr | —CH₂CH₂S—CO-i-Pr | Me | N |
| 526 | Et | i-Pr | —CH₂CH₂S—CO-i-Pr | —CH₂CH₂S—CO-i-Pr | Me | N |
| 527 | Et | n-Bu | —CH₂CH₂S—CO-i-Pr | —CH₂CH₂S—CO-i-Pr | Me | N |
| 528 | n-Pr | n-Pr | —CH₂CH₂S—CO-i-Pr | —CH₂CH₂S—CO-i-Pr | Me | N |
| 529 | H | Me | —CH₂CH₂S—CO-i-Pr | —CH₂CH₂S—CO-i-Pr | —CH₂F | C |
| 530 | H | Et | —CH₂CH₂S—CO-i-Pr | —CH₂CH₂S—CO-i-Pr | —CH₂F | C |
| 531 | H | n-Pr | —CH₂CH₂S—CO-i-Pr | —CH₂CH₂S—CO-i-Pr | —CH₂F | C |
| 532 | H | i-Pr | —CH₂CH₂S—CO-i-Pr | —CH₂CH₂S—CO-i-Pr | —CH₂F | C |
| 533 | H | n-Bu | —CH₂CH₂S—CO-i-Pr | —CH₂CH₂S—CO-i-Pr | —CH₂F | C |
| 534 | H | Me | —CH₂CH₂S—CO-i-Pr | —CH₂CH₂S—CO-i-Pr | —CH₂F | N |
| 535 | H | Et | —CH₂CH₂S—CO-i-Pr | —CH₂CH₂S—CO-i-Pr | —CH₂F | N |
| 536 | H | n-Pr | —CH₂CH₂S—CO-i-Pr | —CH₂CH₂S—CO-i-Pr | —CH₂F | N |
| 537 | H | i-Pr | —CH₂CH₂S—CO-i-Pr | —CH₂CH₂S—CO-i-Pr | —CH₂F | N |
| 538 | H | n-Bu | —CH₂CH₂S—CO-i-Pr | —CH₂CH₂S—CO-i-Pr | —CH₂F | N |
| 539 | Me | Me | —CH₂CH₂S—CO-i-Pr | —CH₂CH₂S—CO-i-Pr | —CH₂F | C |
| 540 | Me | Et | —CH₂CH₂S—CO-i-Pr | —CH₂CH₂S—CO-i-Pr | —CH₂F | C |
| 541 | Me | n-Pr | —CH₂CH₂S—CO-i-Pr | —CH₂CH₂S—CO-i-Pr | —CH₂F | C |

TABLE 1-continued

| Compound No. | R¹ | R² | R³ | R⁴ | R⁵ | X |
|---|---|---|---|---|---|---|
| 542 | Me | i-Pr | —CH₂CH₂S—CO-i-Pr | —CH₂CH₂S—CO-i-Pr | —CH₂F | C |
| 543 | Me | n-Bu | —CH₂CH₂S—CO-i-Pr | —CH₂CH₂S—CO-i-Pr | —CH₂F | C |
| 544 | Et | Et | —CH₂CH₂S—CO-i-Pr | —CH₂CH₂S—CO-i-Pr | —CH₂F | C |
| 545 | Et | n-Pr | —CH₂CH₂S—CO-i-Pr | —CH₂CH₂S—CO-i-Pr | —CH₂F | C |
| 546 | Et | i-Pr | —CH₂CH₂S—CO-i-Pr | —CH₂CH₂S—CO-i-Pr | —CH₂F | C |
| 547 | Et | n-Bu | —CH₂CH₂S—CO-i-Pr | —CH₂CH₂S—CO-i-Pr | —CH₂F | C |
| 548 | n-Pr | n-Pr | —CH₂CH₂S—CO-i-Pr | —CH₂CH₂S—CO-i-Pr | —CH₂F | C |
| 549 | Me | Me | —CH₂CH₂S—CO-i-Pr | —CH₂CH₂S—CO-i-Pr | —CH₂F | N |
| 550 | Me | Et | —CH₂CH₂S—CO-i-Pr | —CH₂CH₂S—CO-i-Pr | —CH₂F | N |
| 551 | Me | n-Pr | —CH₂CH₂S—CO-i-Pr | —CH₂CH₂S—CO-i-Pr | —CH₂F | N |
| 552 | Me | i-Pr | —CH₂CH₂S—CO-i-Pr | —CH₂CH₂S—CO-i-Pr | —CH₂F | N |
| 553 | Me | n-Bu | —CH₂CH₂S—CO-i-Pr | —CH₂CH₂S—CO-i-Pr | —CH₂F | N |
| 554 | Et | Et | —CH₂CH₂S—CO-i-Pr | —CH₂CH₂S—CO-i-Pr | —CH₂F | N |
| 555 | Et | n-Pr | —CH₂CH₂S—CO-i-Pr | —CH₂CH₂S—CO-i-Pr | —CH₂F | N |
| 556 | Et | i-Pr | —CH₂CH₂S—CO-i-Pr | —CH₂CH₂S—CO-i-Pr | —CH₂F | N |
| 557 | Et | n-Bu | —CH₂CH₂S—CO-i-Pr | —CH₂CH₂S—CO-i-Pr | —CH₂F | N |
| 558 | n-Pr | n-Pr | —CH₂CH₂S—CO-i-Pr | —CH₂CH₂S—CO-i-Pr | —CH₂F | N |
| 559 | H | Me | —CH₂CH₂S—CO-i-Pr | —CH₂CH₂S—CO-i-Pr | —CH₂OH | C |
| 560 | H | Et | —CH₂CH₂S—CO-i-Pr | —CH₂CH₂S—CO-i-Pr | —CH₂OH | C |
| 561 | H | n-Pr | —CH₂CH₂S—CO-i-Pr | —CH₂CH₂S—CO-i-Pr | —CH₂OH | C |
| 562 | H | i-Pr | —CH₂CH₂S—CO-i-Pr | —CH₂CH₂S—CO-i-Pr | —CH₂OH | C |
| 563 | H | n-Bu | —CH₂CH₂S—CO-i-Pr | —CH₂CH₂S—CO-i-Pr | —CH₂OH | C |
| 564 | H | Me | —CH₂CH₂S—CO-i-Pr | —CH₂CH₂S—CO-i-Pr | —CH₂OH | N |
| 565 | H | Et | —CH₂CH₂S—CO-i-Pr | —CH₂CH₂S—CO-i-Pr | —CH₂OH | N |
| 566 | H | n-Pr | —CH₂CH₂S—CO-i-Pr | —CH₂CH₂S—CO-i-Pr | —CH₂OH | N |
| 567 | H | i-Pr | —CH₂CH₂S—CO-i-Pr | —CH₂CH₂S—CO-i-Pr | —CH₂OH | N |
| 568 | H | n-Bu | —CH₂CH₂S—CO-i-Pr | —CH₂CH₂S—CO-i-Pr | —CH₂OH | N |
| 569 | Me | Me | —CH₂CH₂S—CO-i-Pr | —CH₂CH₂S—CO-i-Pr | —CH₂OH | C |
| 570 | Me | Et | —CH₂CH₂S—CO-i-Pr | —CH₂CH₂S—CO-i-Pr | —CH₂OH | C |
| 571 | Me | n-Pr | —CH₂CH₂S—CO-i-Pr | —CH₂CH₂S—CO-i-Pr | —CH₂OH | C |
| 572 | Me | i-Pr | —CH₂CH₂S—CO-i-Pr | —CH₂CH₂S—CO-i-Pr | —CH₂OH | C |
| 573 | Me | n-Bu | —CH₂CH₂S—CO-i-Pr | —CH₂CH₂S—CO-i-Pr | —CH₂OH | C |
| 574 | Et | Et | —CH₂CH₂S—CO-i-Pr | —CH₂CH₂S—CO-i-Pr | —CH₂OH | C |
| 575 | Et | n-Pr | —CH₂CH₂S—CO-i-Pr | —CH₂CH₂S—CO-i-Pr | —CH₂OH | C |
| 576 | Et | i-Pr | —CH₂CH₂S—CO-i-Pr | —CH₂CH₂S—CO-i-Pr | —CH₂OH | C |
| 577 | Et | n-Bu | —CH₂CH₂S—CO-i-Pr | —CH₂CH₂S—CO-i-Pr | —CH₂OH | C |
| 578 | n-Pr | n-Pr | —CH₂CH₂S—CO-i-Pr | —CH₂CH₂S—CO-i-Pr | —CH₂OH | C |
| 579 | Me | Me | —CH₂CH₂S—CO-i-Pr | —CH₂CH₂S—CO-i-Pr | —CH₂OH | N |
| 580 | Me | Et | —CH₂CH₂S—CO-i-Pr | —CH₂CH₂S—CO-i-Pr | —CH₂OH | N |
| 581 | Me | n-Pr | —CH₂CH₂S—CO-i-Pr | —CH₂CH₂S—CO-i-Pr | —CH₂OH | N |
| 582 | Me | i-Pr | —CH₂CH₂S—CO-i-Pr | —CH₂CH₂S—CO-i-Pr | —CH₂OH | N |
| 583 | Me | n-Bu | —CH₂CH₂S—CO-i-Pr | —CH₂CH₂S—CO-i-Pr | —CH₂OH | N |
| 584 | Et | Et | —CH₂CH₂S—CO-i-Pr | —CH₂CH₂S—CO-i-Pr | —CH₂OH | N |
| 585 | Et | n-Pr | —CH₂CH₂S—CO-i-Pr | CH₂CH₂S—CO-i-Pr | —CH₂OH | N |
| 586 | Et | i-Pr | —CH₂CH₂S—CO-i-Pr | —CH₂CH₂S—CO-i-Pr | —CH₂OH | N |
| 587 | Et | n-Bu | —CH₂CH₂S—CO-i-Pr | —CH₂CH₂S—CO-i-Pr | —CH₂OH | N |
| 588 | n-Pr | n-Pr | —CH₂CH₂S—CO-i-Pr | —CH₂CH₂S—CO-i-Pr | —CH₂OH | N |
| 589 | H | Ph | —CH₂OCO-t-Bu | —CH₂OCO-t-Bu | Me | C |
| 590 | H | Ph | —CH₂OCO-t-Bu | —CH₂OCO-t-Bu | —CH₂F | C |
| 591 | H | Ph | —CH₂OCO-t-Bu | —CH₂OCO-t-Bu | —CH₂OH | C |
| 592 | H | Ph | —CH₂OCO-t-Bu | —CH₂OCO-t-Bu | Me | N |
| 593 | H | Ph | —CH₂OCO-t-Bu | —CH₂OCO-t-Bu | —CH₂F | N |
| 594 | H | Ph | —CH₂OCO-t-Bu | —CH₂OCO-t-Bu | —CH₂OH | N |
| 595 | Me | Ph | —CH₂OCO-t-Bu | —CH₂OCO-t-Bu | Me | C |
| 596 | Me | Ph | —CH₂OCO-t-Bu | —CH₂OCO-t-Bu | —CH₂F | C |
| 597 | Me | Ph | —CH₂OCO-t-Bu | —CH₂OCO-t-Bu | —CH₂OH | C |
| 598 | Me | Ph | —CH₂OCO-t-Bu | —CH₂OCO-t-Bu | Me | N |
| 599 | Me | Ph | —CH₂OCO-t-Bu | —CH₂OCO-t-Bu | —CH₂F | N |
| 600 | Me | Ph | —CH₂OCO-t-Bu | —CH₂OCO-t-Bu | —CH₂OH | N |
| 601 | H | Ph | —CH₂CH₂S—CO-i-Pr | —CH₂CH9S-CO-i-Pr | Me | C |
| 602 | H | Ph | —CH₂CH₂S—CO-i-Pr | —CH₂CH9S-CO-i-Pr | —CH₂F | C |
| 603 | H | Ph | —CH₂CH₂S—CO-i-Pr | —CH₂CH₂S—CO-i-Pr | —CH₂OH | C |
| 604 | H | Ph | —CH₂CH₂S—CO-i-Pr | —CH₂CH₂S—CO-i-Pr | Me | N |
| 605 | H | Ph | —CH₂CH₂S—CO-i-Pr | —CH₂CH₂S—CO-i-Pr | —CH₂F | N |
| 606 | H | Ph | —CH₂CH₂S—CO-i-Pr | —CH₂CH₂S—CO-i-Pr | —CH₂OH | N |
| 607 | Me | Ph | —CH₂CH₂S—CO-i-Pr | —CH₂CH₂S—CO-i-Pr | Me | C |
| 608 | Me | Ph | —CH₂CH₂S—CO-i-Pr | —CH₂CH₂S—CO-i-Pr | —CH₂F | C |
| 609 | Me | Ph | —CH₂CH₂S—CO-i-Pr | —CH₂CH₂S—CO-i-Pr | —CH₂OH | C |
| 610 | Me | Ph | —CH₂CH₂S—CO-i-Pr | —CH₂CH₂S—CO-i-Pr | Me | N |
| 611 | Me | Ph | —CH₂CH₂S—CO-i-Pr | —CH₂CH₂S—CO-i-Pr | —CH₂F | N |
| 612 | Me | Ph | —CH₂CH₂S—CO-i-Pr | —CH₂CH₂S—CO-i-Pr | —CH₂OH | N |
| 613 | H | Ph | CF₃CH₂— | CF₃CH₂— | H | C |
| 614 | H | Ph | H | CF₃CH₂— | H | C |
| 615 | H | Ph | Me | CF₃CH₂— | H | C |
| 616 | H | Ph | H | H | H | C |

TABLE 1-continued

| Compound No. | R¹ | R² | R³ | R⁴ | R⁵ | X |
|---|---|---|---|---|---|---|
| 617 | H | Ph | CF₃CH₂— | CF₃CH₂— | H | N |
| 618 | H | Ph | Me | CF₃CH₂— | H | N |
| 619 | H | Ph | H | CF₃CH₂— | H | N |
| 620 | H | Ph | H | H | H | N |
| 621 | Me | Ph | CF₃CH₂— | CF₃CH₂— | H | C |
| 622 | Me | Ph | Me | CF₃CH₂— | H | C |
| 623 | Me | Ph | H | CF₃CH₂— | H | C |
| 624 | Me | Ph | H | H | H | C |
| 625 | Me | Ph | CF₃CH₂— | CF₃CH₂— | H | N |
| 626 | Me | Ph | Me | CF₃CH₂— | H | N |
| 627 | Me | Ph | H | CF₃CH₂— | H | N |
| 628 | Me | Ph | H | H | H | N |
| 629 | H | Me | CF₃CH₂— | CF₃CH₂— | Me | C |
| 630 | H | Et | CF₃CH₂— | CF₃CH₂— | Me | C |
| 631 | H | n-Pr | CF₃CH₂— | CF₃CH₂— | Me | C |
| 632 | H | i-Pr | CF₃CH₂— | CF₃CH₂— | Me | C |
| 633 | H | n-Bu | CF₃CH₂— | CF₃CH₂— | Me | C |
| 634 | H | Me | CF₃CH₂— | CF₃CH₂— | Me | N |
| 635 | H | Et | CF₃CH₂— | CF₃CH₂— | Me | N |
| 636 | H | n-Pr | CF₃CH₂— | CF₃CH₂— | Me | N |
| 637 | H | i-Pr | CF₃CH₂— | CF₃CH₂— | Me | N |
| 638 | H | n-Bu | CF₃CH₂— | CF₃CH₂— | Me | N |
| 639 | Me | Me | CF₃CH₂— | CF₃CH₂— | Me | C |
| 640 | Me | Et | CF₃CH₂— | CF₃CH₂— | Me | C |
| 641 | Me | n-Pr | CF₃CH₂— | CF₃CH₂— | Me | C |
| 642 | Me | i-Pr | CF₃CH₂— | CF₃CH₂— | Me | C |
| 643 | Me | n-Bu | CF₃CH₂— | CF₃CH₂— | Me | C |
| 644 | Et | Et | CF₃CH₂— | CF₃CH₂— | Me | C |
| 645 | Et | n-Pr | CF₃CH₂— | CF₃CH₂— | Me | C |
| 646 | Et | i-Pr | CF₃CH₂— | CF₃CH₂— | Me | C |
| 647 | Et | n-Bu | CF₃CH₂— | CF₃CH₂— | Me | C |
| 648 | n-Pr | n-Pr | CF₃CH₂— | CF₃CH₂— | Me | C |
| 649 | Me | Me | CF₃CH₂— | CF₃CH₂— | Me | N |
| 650 | Me | Et | CF₃CH₂— | CF₃CH₂— | Me | N |
| 651 | Me | n-Pr | CF₃CH₂— | CF₃CH₂— | Me | N |
| 652 | Me | i-Pr | CF₃CH₂— | CF₃CH₂— | Me | N |
| 653 | Me | n-Bu | CF₃CH₂— | CF₃CH₂— | Me | N |
| 654 | Et | Et | CF₃CH₂— | CF₃CH₂— | Me | N |
| 655 | Et | n-Pr | CF₃CH₂— | CF₃CH₂— | Me | N |
| 656 | Et | i-Pr | CF₃CH₂— | CF₃CH₂— | Me | N |
| 657 | Et | n-B.u | CF₃CH₂— | CF₃CH₂— | Me | N |
| 658 | n-Pr | n-Pr | CF₃CH₂— | CF₃CH₂— | Me | N |
| 659 | H | Me | Me | CF₃CH₂— | Me | C |
| 660 | H | Et | Me | CF₃CH₂— | Me | C |
| 661 | H | n-Pr | Me | CF₃CH₂— | Me | C |
| 662 | H | i-Pr | Me | CF₃CH₂— | Me | C |
| 663 | H | n-Bu | Me | CF₃CH₂— | Me | C |
| 664 | H | Me | Me | CF₃CH₂— | Me | N |
| 665 | H | Et | Me | CF₃CH₂— | Me | N |
| 666 | H | n-Pr | Me | CF₃CH₂— | Me | N |
| 667 | H | i-Pr | Me | CF₃CH₂— | Me | N |
| 668 | H | n-Bu | Me | CF₃CH₂— | Me | N |
| 669 | Me | Me | Me | CF₃CH₂— | Me | C |
| 670 | Me | Et | Me | CF₃CH₂— | Me | C |
| 671 | Me | n-Pr | Me | CF₃CH₂— | Me | C |
| 672 | Me | i-Pr | Me | CF₃CH₂— | Me | C |
| 673 | Me | n-Bu | Me | CF₃CH₂— | Me | C |
| 674 | Et | Et | Me | CF₃CH₂— | Me | C |
| 675 | Et | n-Pr | Me | CF₃CH₂— | Me | C |
| 676 | Et | i-Pr | Me | CF₃CH₂— | Me | C |
| 677 | Et | n-Bu | Me | CF₃CH₂— | Me | C |
| 678 | n-Pr | n-Pr | Me | CF₃CH₂— | Me | C |
| 679 | Me | Me | Me | CF₃CH₂— | Me | N |
| 680 | Me | Et | Me | CF₃CH₂— | Me | N |
| 681 | Me | n-Pr | Me | CF₃CH₂— | Me | N |
| 682 | Me | i-Pr | Me | CF₃CH₂— | Me | N |
| 683 | Me | n-Bu | Me | CF₃CH₂— | Me | N |
| 684 | Et | Et | Me | CF₃CH₂— | Me | N |
| 685 | Et | n-Pr | Me | CF₃CH₂— | Me | N |
| 686 | Et | i-Pr | Me | CF₃CH₂— | Me | N |
| 687 | Et | n-Bu | Me | CF₃CH₂— | Me | N |
| 688 | n-Pr | n-Pr | Me | CF₃CH₂— | Me | N |
| 689 | H | Me | CF₃CH₂— | H | Me | C |
| 690 | H | Et | CF₃CH₂— | H | Me | C |
| 691 | H | n-Pr | CF₃CH₂— | H | Me | C |

TABLE 1-continued

| Compound No. | R¹ | R² | R³ | R⁴ | R⁵ | X |
|---|---|---|---|---|---|---|
| 692 | H | i-Pr | CF₃CH₂— | H | Me | C |
| 693 | H | n-Bu | CF₃CH₂— | H | Me | C |
| 694 | H | Me | CF₃CH₂— | H | Me | N |
| 695 | H | Et | CF₃CH₂— | H | Me | N |
| 696 | H | n-Pr | CF₃CH₂— | H | Me | N |
| 697 | H | i-Pr | CF₃CH₂— | H | Me | N |
| 698 | H | n-Bu | CF₃CH₂— | H | Me | N |
| 699 | Me | Me | CF₃CH₂— | H | Me | C |
| 700 | Me | Et | CF₃CH₂— | H | Me | C |
| 701 | Me | n-Pr | CF₃CH₂— | H | Me | C |
| 702 | Me | i-Pr | CF₃CH₂— | H | Me | C |
| 703 | Me | n-Bu | CF₃CH₂— | H | Me | C |
| 704 | Et | Et | CF₃CH₂— | H | Me | C |
| 705 | Et | n-Pr | CF₃CH₂— | H | Me | C |
| 706 | Et | i-Pr | CF₃CH₂— | H | Me | C |
| 707 | Et | n-Bu | CF₃CH₂— | H | Me | C |
| 708 | n-Pr | n-Pr | CF₃CH₂— | H | Me | C |
| 709 | Me | Me | CF₃CH₂— | H | Me | N |
| 710 | Me | Et | CF₃CH₂— | H | Me | N |
| 711 | Me | n-Pr | CF₃CH₂— | H | Me | N |
| 712 | Me | i-Pr | CF₃CH₂— | H | Me | N |
| 713 | Me | n-Bu | CF₃CH₂— | H | Me | N |
| 714 | Et | Et | CF₃CH₂— | H | Me | N |
| 715 | Et | n-Pr | CF₃CH₂— | H | Me | N |
| 716 | Et | i-Pr | CF₃CH₂— | H | Me | N |
| 717 | Et | n-Bu | CF₃CH₂— | H | Me | N |
| 718 | n-Pr | n-Pr | CF₃CH₂— | H | Me | N |
| 719 | H | Me | H | H | Me | C |
| 720 | H | Et | H | H | Me | C |
| 721 | H | n-Pr | H | H | Me | C |
| 722 | H | i-Pr | H | H | Me | C |
| 723 | H | n-Bu | H | H | Me | C |
| 724 | H | Me | H | H | Me | N |
| 725 | H | Et | H | H | Me | N |
| 726 | H | n-Pr | H | H | Me | N |
| 727 | H | i-Pr | H | H | Me | N |
| 728 | H | n-Bu | H | H | Me | N |
| 729 | Me | Me | H | H | Me | C |
| 730 | Me | Et | H | H | Me | C |
| 731 | Me | n-Pr | H | H | Me | C |
| 732 | Me | i-Pr | H | H | Me | C |
| 733 | Me | n-Bu | H | H | Me | C |
| 734 | Et | Et | H | H | Me | C |
| 735 | Et | n-Pr | H | H | Me | C |
| 736 | Et | i-Pr | H | H | Me | C |
| 737 | Et | n-Bu | H | H | Me | C |
| 738 | n-Pr | n-Pr | H | H | Me | C |
| 739 | Me | Me | H | H | Me | N |
| 740 | Me | Et | H | H | Me | N |
| 741 | Me | n-Pr | H | H | Me | N |
| 742 | Me | i-Pr | H | H | Me | N |
| 743 | Me | n-Bu | H | H | Me | N |
| 744 | Et | Et | H | H | Me | N |
| 745 | Et | n-Pr | H | H | Me | N |
| 746 | Et | i-Pr | H | H | Me | N |
| 747 | Et | n-Bu | H | H | Me | N |
| 748 | n-Pr | n-Pr | H | H | Me | N |
| 749 | H | Ph | CF₃CH₂— | CF₃CH₂— | Me | C |
| 750 | H | Ph | H | CF₃CH₂— | Me | C |
| 751 | H | Ph | Me | CF₃CH₂— | Me | C |
| 752 | H | Ph | H | H | Me | C |
| 753 | H | Ph | CF₃CH₂— | CF₃CH₂— | Me | N |
| 754 | H | Ph | Me | CF₃CH₂— | Me | N |
| 755 | H | Ph | H | CF₃CH₂— | Me | N |
| 756 | H | Ph | H | H | Me | N |
| 757 | Me | Ph | CF₃CH₂— | CF₃CH₂— | Me | C |
| 758 | Me | Ph | Me | CF₃CH₂— | Me | C |
| 759 | Me | Ph | H | CF₃CH₂— | Me | C |
| 760 | Me | Ph | H | H | Me | C |
| 761 | Me | Ph | CF₃CH₂— | CF₃CH₂— | Me | N |
| 762 | Me | Ph | Me | CF₃CH₂— | Me | N |
| 763 | Me | Ph | H | CF₃CH₂— | Me | N |
| 764 | Me | Ph | H | H | Me | N |

Methods for preparing the compounds of the present invention will be explained below. Among the compounds represented by the general formula (I), the compounds wherein $R^3$ and $R^4$ are a $C_1$–$C_6$ alkyl group or an ethyl group substituted with one or more halogen atoms can be prepared, for example, according to Reaction Route (1) or (2) set out below

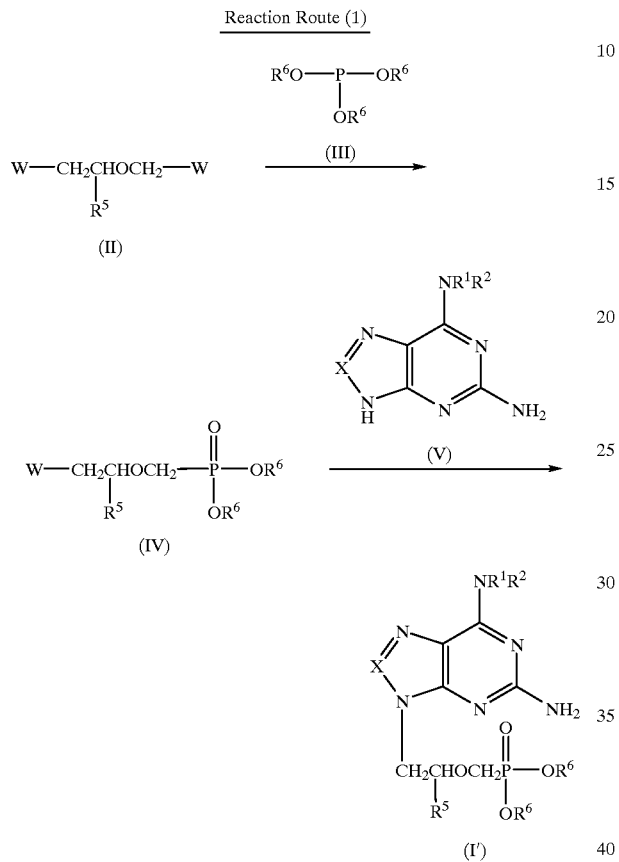

In the above scheme, $R^1$, $R^2$, $R^5$, and X have the same meanings as those defined above, and $R^6$ represents a $C_1$–$C_4$ alkyl group or an ethyl group substituted with one or more halogen atoms. "W" represents a leaving group such as a halogen atom, p-toluenesulfonyloxy group, methanesulfonyloxy group, or trifluoromethanesulfonyloxy group.

A compound of the above general formula (II) and a compound of the above general formula (III) are first allowed to react with each other at a temperature of 10–250° C., preferably 130–180° C. for 0.1–20 hours, preferably 3–6 hours. A compound of the above general formula (IV) obtained by the above reaction can be separated and purified according to an ordinary means for separation and purification such as distillation, adsorption or partition chromatography, if necessary. The compound of the above general formula (IV) can be used for the next step after separation and purification as explained above, or alternatively, the product may be subjected to the following reaction without purification.

The compound of the above general formula (IV) is then allowed to react with a compound of the above general formula (V) at a temperature of 10–200° C., preferably 50–150° C. for 0.1–100 hours, preferably 5–20 hours in a suitable solvent such as acetonitrile, tetrahydrofuran, dimethyl sulfoxide, dimethylformamide, or methylpyrrolidone in the presence of a base such as sodium carbonate, potassium carbonate, cesium carbonate, sodium hydride, potassium hydride, triethylamine, or diazabicycloundecene to obtain a compound of the above general formula (I').

Sources of the compound of the above general formula (II) as the starting material for Reaction Route (1), the compound of the above general formula (III), and the compound of the above general formula (IV) are not particularly limited. Those commercially available as reagents can be used, or those synthesized by a method known, per se, can also be used. A compound of the general formula (V) can be obtained by heating a compound of the general formula (VI) and a compound of the general formula (VIII), which are mentioned later, at a temperature of 50–100° C. in a suitable solvent such as acetonitrile or dimethyl sulfoxide.

The compound of the above general formula (I') can also be prepared by the method set out below.

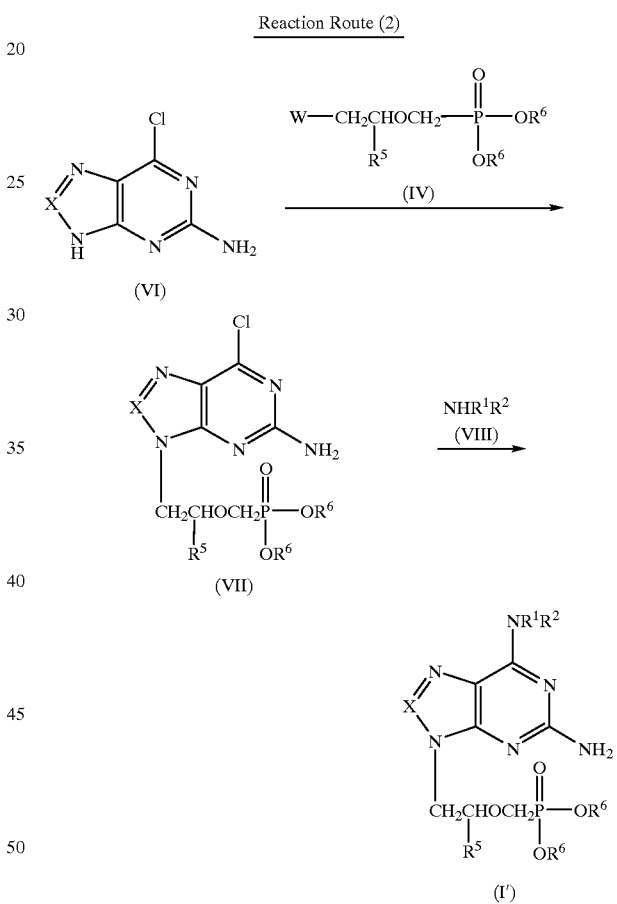

In the above general formulas $R^1$, $R^2$, $R^5$, $R^6$, X, and W have the same meanings as those defined above.

The compound of the above general formula (IV) obtained in Reaction Route (1) and a compound of the above general formula (VI) are allowed to react with each other at a temperature of 10–200° C., preferably 50–150° C. for 0.1–100 hours, preferably 5–20 hours in a suitable solvent such as acetonitrile, tetrahydrofuran, dimethyl sulfoxide, dimethylformamide, or methylpyrrolidone in the presence of a base such as sodium carbonate, potassium carbonate, cesium carbonate, sodium hydride, potassium hydride, triethylamine, or diazabicycloundecene to obtain a compound of the above general formula (VII).

The compound of the above general formula (VII) can be allowed to react with an amine represented by the above general formula (VIII) or hydrochloride thereof at a temperature of 10–200° C., preferably 70–120° C. for 0.1–100 hours, preferably 5–12 hours in a suitable solvent such as acetonitrile, tetrahydrofuran, dimethyl sulfoxide, dimethylformamide, or methylpyrrolidone optionally in the presence of a suitable tertiary amine to obtain a compound of the above general formula (I'). The compound of the above general formula (I') corresponds to a compound of the general formula (I) wherein each of $R^3$ and $R^4$ is a $C_1$–$C_6$ alkyl group or an ethyl group substituted with one or more halogen atoms.

Sources of the compound of the above general formula (VI) as the starting material for Reaction Route (2) are not particularly limited. Those commercially available as reagents may be used, or those synthesized by a method known per se may also be used.

The compound of the general formula (I') is further reacted to obtain a compound of the general formula (I) having a substituent other than $R^6$ of the compound of the general formula (I').

A compound of the general formula (1) wherein $R^3$ and $R^4$ are hydrogen atoms can be obtained by hydrolyzing the compound of the above general formula (I').

A compound of the general formula (I) wherein $R^3$ is hydrogen atom, a $C_1$–$C_6$ alkyl group, an acylthioethyl group, or an ethyl group substituted with one or more halogen atoms, and $R^4$ is a $C_1$–$C_6$ alkyl group or an ethyl group substituted with one or more halogen atoms can be prepared by reacting the compound of the above general formula (I') with a compound of the general formula $R^7OH$ (IX) wherein $R^7$ represents hydrogen atom, a $C_1$–$C_4$ alkyl group, an acylthioethyl group, or an ethyl group substituted with one or more halogen atoms at a temperature of 10–100° C., preferably 20–30° C. for 0.1–100 hours, preferably 5–12 hours without solvent or in a suitable solvent, for example, chlorine-containing solvent such as dichloromethane, pyridine, acetonitrile, tetrahydrofuran, dimethyl sulfoxide, dimethylformamide, or methylpyrrolidone, and optionally in the presence of an acid such as p-toluenesulfonic acid, methanesulfonic acid, hydrochloric acid, or phosphoric acid.

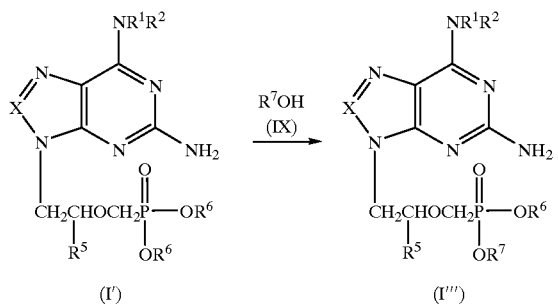

The compounds of the general formula (I) wherein $R^3$ and $R^4$ each independently represent hydrogen atom, a $C_1$–$C_6$ alkyl group, an acylthioethyl group, or an ethyl group substituted with one or more halogen atoms can be obtained according to the method set out below.

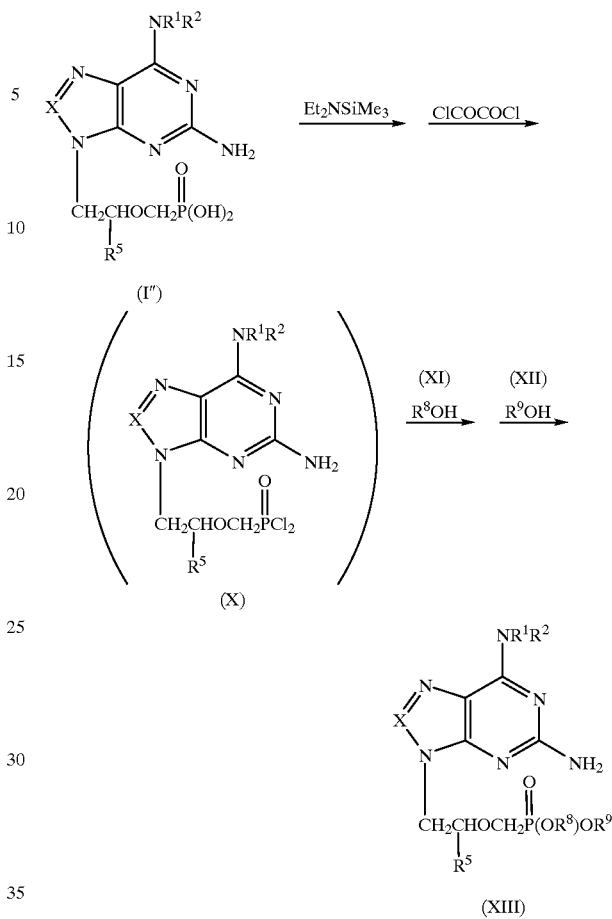

In the above general formulas, $R^1$, $R^2$, $R^5$, and X have the same meanings as those defined above, and $R^8$ and $R^9$ each independently represent a $C_1$–$C_4$ alkyl group, an acylthioethyl group, or an ethyl group substituted with one or more halogen atoms.

A compound of the above general formula (I") is first reacted with trimethylsilyldiethylamine at a temperature around room temperature for about one hour in a suitable solvent, for example, a chlorine-containing solvent such as dichloromethane, dichloroethane, or chloroform. For this reaction, 2 moles or more of trimethylsilyldiethylamine should be used per 1 mole of the compound of the above general formula (I"). Then, the reaction mixture is concentrated to dryness, and the resulting residue is dissolved in a suitable solvent, for example, a chlorine-containing solvent such as dichloromethane. To this solution, 2 moles or more of oxalyl chloride per 1 mole of the compound of above general formula (I") is added, and the mixture is allowed to react for about 1 hour under ice cooling and then for about 1 hour at room temperature in the presence of catalytic amount of dimethylformamide.

After evaporating the solvent, the resulting compound of the above general formula (X), usually without further purification, is allowed to react with a compound of the general formula (XI) and/or a compound of the general formula (XII) at a temperature of 10–100° C., preferably 20–30° C. for 0.1–100 hours, preferably 5–12 hours in a suitable solvent such as chlorine-containing solvent such as dichloromethane, pyridine, acetonitrile, tetrahydrofuran, dimethyl sulfoxide, dimethylformamide and methylpyrrolidone. The resulting compound of the general formula (XIII) corresponds to a compound of the general formula (I) wherein each of $R^3$ and $R^4$ independently represents hydrogen atom, a $C_1$–$C_4$ alkyl group, an acylthioethyl group, or an ethyl group substituted with one or more halogen atoms.

The compounds of the above general formula (I") used as the starting material for the above reaction can be obtained by hydrolyzing compounds of general formula (I'), as already explained above, or they can be efficiently obtained by preparing compounds of the above general formula (I') from compounds of the above general formula (IV) wherein $R^6$ is a $C_1$–$C_4$ alkyl group, and then reacting the resulting product with triethyliodosilane, trimethylbromosilane or the like.

A compound of general formula (I) wherein each of $R^3$ and $R^4$ is an acyloxymethyl group can be obtained by reacting a compound of the general formula (I") with an acyloxymethyl halide represented by the general formula: $R^{10}Y$ (XIV) wherein $R^{10}$ represents an acyloxymethyl group, and Y represents chlorine atom, bromine atom or iodine atom, at a temperature of 0–200° C., preferably 10–100° C. for 1–300 hours, preferably 10–200 hours in a suitable solvent such as acetonitrile, tetrahydrofuran, dimethyl sulfoxide, dimethylformamide, or methylpyrrolidone in the presence of a base such as sodium carbonate, potassium carbonate, cesium carbonate, sodium hydride, potassium hydride, triethylamine, pyridine, diazabicycloundecene, or N,N'-dicyclohexyl-4-morpholinecarboxamidine.

The compound of the above general formula (I) obtained as described above can be separated from a reaction mixture and purified, if necessary, by applying an ordinary method for separation and purification of a nucleotide compound which can be suitably chosen from, for example, recrystallization, adsorption chromatography, ion exchange chromatography, partition chromatography and the like.

The compounds of the present invention have antiviral activity, as demonstrated in the test examples described later, and are expected to have antitumor activity in the same manner as other ionic phosphonate nucleotide analogues. Target viruses are not particularly limited. Specific examples include RNA viruses such as human immunodeficiency virus, influenza virus and hepatitis C virus, and DNA viruses such as herpes simplex virus I, herpes simplex virus II, cytomegalovirus, herpes zoster varicellosus virus, and hepatitis B virus, and a preferred example includes hepatitis B virus.

When the compound of the present invention or a pharmaceutically acceptable salt thereof, or a hydrate or a solvate thereof is used as medicaments, the substance, per se, can be administered, or administered as a pharmaceutical composition prepared in combination with a pharmaceutically acceptable carrier. A sort of the pharmaceutical composition can be decided depending on solubility and chemical properties of the substance, route of administration, dosage regimen and the like. For example, the pharmaceutical composition can be orally administered as a formulation such as, for example, granules, fine granules, powders, tablets, hard syrups, soft capsules, troches, syrups, emulsions, soft gelatin capsules, gels, pastes, suspensions, or liposome formulations, or administered intravenously, intramuscularly, or subcutaneously as an injection. The pharmaceutical composition may also be formulated as a powder for injection, and administered as an injection prepared upon use.

The pharmaceutically acceptable carriers include organic or inorganic solids or liquids for manufacturing pharmaceutical preparations suitable for oral, enteral, parenteral, or topical administration. Examples of the solid carriers for manufacturing solid pharmaceutical compositions include, for example, lactose, sucrose, starch, talc, cellulose, dextrin, kaolin, calcium carbonate, agar, pectin, stearic acid, magnesium stearate, lecithin, sodium chloride and the like. Examples of the liquid carrier for manufacturing liquid pharmaceutical compositions for oral administration include glycerin, peanut oil, polyvinylpyrrolidone, olive oil, ethanol, benzyl alcohol, propylene glycol, physiological saline, water and the like.

The pharmaceutical composition of the present invention may also contain auxiliaries other than the carrier mentioned above, for example, moistening agents, suspending aids, sweeteners, aromatics, colorants, preservatives and the like. Liquid pharmaceutical compositions may be encapsulated in capsules made of absorbable material such as gelatin and administered as capsules. Solvent or suspending medium used for the preparation of pharmaceutical compositions for parenteral administration, i.e., injection or the like, may be, for example, water, propylene glycol, polyethylene glycol, benzyl alcohol, ethyl oleate, lecithin or the like.

The compounds of the present invention, in particular, ester derivatives represented by the above general formula (I') have high oral absorbability, as demonstrated in the test examples described later, and accordingly, pharmaceutical compositions for oral administration are preferred compositions among the pharmaceutical compositions of the present invention. The aforementioned pharmaceutical compositions can be prepared according to ordinary and conventional methods.

Dose may generally be within the range of 1–500 mg/kg, preferably 5–50 mg/kg for an adult based on the compound of the present invention as an active ingredient, when the medicament is administered orally. However, the dose may be appropriately increased or decreased for an administration depending on, for example, age, symptoms, and conditions of a patient, or a use or no use of other drug administered in combination. The aforementioned daily dose may be administered once a day, or the dose may be divided into two or several portions and administered with appropriate intervals. In addition, an administration can be performed intermittently. When used as injection, daily dose may generally be within the range of 0.1–50 mg/kg, preferably 0.1–5 mg/kg for an adult based the compound of the present invention as an active ingredient.

EXAMPLES

The present invention will be further explained more specifically by referring to the following examples. However, the scope of the present invention is not limited to the following examples.

Example 1

Preparation of 2-amino-9-[2-[bis(2,2,2-trifluoroethyl) phosphonylmethoxy]-ethyl]-6-(dimethylamino)purine (Compound No. 11 in Table 1)

2-Chloroethyl chloromethyl ether (87 g, 670 mmol) and tris(2,2,2-trifluoroethyl)phosphite (200 g, 610 mmol) were allowed to react at 160° C. for seven hours to obtain 2-[bis(2,2,2-trifluoroethyl)phosphonylmethoxy]ethyl chloride quantitatively.

The 2-[bis(2,2,2-trifluoroethyl)phosphonylmethoxy]ethyl chloride (206 g) was dissolved in methyl ethyl ketone (2000 ml) and the solution was heated under reflux with sodium iodide (270 g) for eight hours. After the reaction was completed, the mixture was cooled to room temperature, and concentrated to dryness. The residue was dissolved in chloroform/hexane and adsorbed on a silica gel in a column, and then eluted with chloroform/hexane to obtain 2-[bis(2,2,2-trifluoroethyl) phosphonylmethoxy] ethyl iodide quantitatively.

2-Amino-6-(dimethylamino)purine (7.1 g, 40 mmol) was suspended in dimethyl sulfoxide (300 ml), and reacted with 1,8-diazabicyclo[5.4.0]undec-7-ene (6.6 ml, 44 mmol) at 100° C. for one hour. Then, 2-[bis(2,2,2-trifluoroethyl) phosphonylmethoxy]-ethyl iodide (11.5 ml) was added to the reaction mixture, and the mixture was allowed to react at 100° C. for two hours. After the reaction was completed, the mixture was cooled to room temperature, and then concentrated to dryness. The residue was dissolved in chloroform and adsorbed on a silica gel in a column, and then eluted with 5%-methanol/chloroform to obtain the title compound (2.35 g, 12%) having the physicochemical properties set out below.

m.p.: 90–92° C. (diisopropyl ether); $^1$H-NMR (CDCl$_3$, δ): 3.45 (s, 6H), 3.96–3.85 (m, 4H), 4.20–4.43 (m, 6H), 4.64 (s, 2H), 7.51 (s, 1H).

Example 2

Preparation of 2-amino-9-[2-[bis(2,2,2-trifluoroethy) phosphonylmethoxy]-ethyl]-6-(dimethylamino)purine (Compound No. 11 in Table 1)

2-Amino-6-chloropurine (15.0 g, 88 mmol) was suspended in dimethylformamide (360 ml), and reacted with 1,8-diazabicyclo[5.4.0]undec-7-ene (13.9 ml, 93 mmol) at 80° C. for one hour. Then, 2-[bis(2,2,2-trifluoroethyl) phosphonylmethoxy]-ethyl iodide (23.8 ml) was added to the reaction mixture, and the mixture was allowed to react at 100° C. for five hours. After the reaction was completed, the mixture was cooled to room temperature and concentrated to dryness. The residue was dissolved in chloroform and adsorbed on a silica gel in a column, and eluted with 5%-methanol/chloroform to obtain 2-amino-9-[2-[bis(2,2,2-trifluoroethyl)phosphonyl-methoxy]ethyl]-6-chloropurine (23.3 g, 56%).

Triethylamine (0.28 ml) and dimethylamine hydrochloride (0.16 g) were added to a solution of the 2-amino-9-[2-[bis(2,2,2-trifluoroethyl)phosphonylmethoxy]ethyl]-6-chloropurine (0.47 g, 1.0 mmol) obtained above in dimethylformamide (4.5 ml), and the mixture was stirred at 100° C. for five hours. The reaction mixture was cooled to room temperature and concentrated to dryness. The residue was dissolved in chloroform and adsorbed on a silica gel in a column, and then eluted with 5%-methanol/chloroform to obtain 2-amino-9-[2-[bis(2,2,2-trifluoroethyl) phosphonylmethoxy]ethyl]-6-(dimethylamino)purine (0.33 g, 69%).

Example 3

Preparation of 2-amino-9-[2-[bis(2,2,2-trifluoroethyl) phosphonylmethoxy]-ethyl]-6-(diethylamino)purine (Compound No. 16 in Table 1)

The title compound having the physicochemical properties set out below was obtained in the same manner as in Example 2, except that diethylamine was used instead of the dimethylamine hydrochloride.

m.p.: 105–106° C. (diusopropyl ether); $^1$H-NMR (CDCl$_3$, δ): 1.24 (t, J=6.9 Hz, 6H), 3.80–4.10 (m, 6H), 4.20–4.48 (m, 6H), 4.54 (s, 2H), 7.51 (s, 1H).

Example 4

Preparation of 2-amino-9-[2-[bis(2,2,2-trifluoroethyl) phosphonylmethoxy]-ethyl]-6-(1,1-dipropylamino)purine (Compound No. 20 in Table 1)

The title compound having the physicochemical properties set out below was obtained as syrup in the same manner as in Example 2, except that 1,1-dipropylamine was used instead of the dimethylamine hydrochloride.

$^1$H-NMR (CDCl$_3$, δ): 0.93 (t, J=7.4 Hz, 6H), 1.68 (tq, J=7.6 Hz, 4H), 3.60–4.10 (m, 8H), 4.17–4.50 (m, 6H), 4.60 (s, 2H), 7.49 (s, 1H).

Example 5

Preparation of 2-amino-9-[2-[bis(2,2,2-trifluoroethyl) phosphonylmethoxy]-ethyl]-6-(methyl-1-propylamino) purine (Compound No. 13 in Table 1)

The title compound having the physicochemical properties set out below was obtained in the same manner as in Example 2, except that methyl-1-propylamine was used instead of the dimethylamine hydrochloride.

m.p.: 88–90° C. (diisopropyl ether); $^1$H-NMR (CDCl$_3$, δ): 0.94 (t, J=7.4 Hz, 6H), 1.55–1.83 (m, 2H), 3.37 (bs, 3H), (m, 6H), 4.20–4.46 (m, 6H), 4.56 (s, 2H), 7.50 (s, 1H).

Example 6

Preparation of 2-amino-8-aza-9-[2-[bis(2,2,2-trifluoroethyl) phosphonyl-methoxy]ethyl]-6-(dimethylamino)purine (Compound No. 21 in Table 1)

The title compound having the physicochemical properties mentioned below was obtained in the same manner as in Example 1, except that 2-amino-8-aza-6-(dimethylamino) purine was used instead of the 2-amino-6-(dimethylamino) purine.

m.p.: 184–187° C. (chloroform); $^1$H-NMR (DMSO-d$_6$, δ): 0.94 (t, J=7.4 Hz, 6H), 1.55–1.83 (m, 2H), 3.37 (bs, 3H), 3.80–4.10 (m, 6H), 4.20–4.46 (m, 6H), 4.56 (s, 2H), 7.50 (s, 1H).

Example 7

Preparation of 2-amino-9-[2-[bis(2,2,2-trifluoroethyl) phosphonylmethoxy]-ethyl]-6-(benzylmethylamino)purine (Compound No. 129 in Table 1)

The title compound having the physicochemical properties set out below was obtained in the same manner as in Example 2, except that benzylmethylamine was used instead of the dimethylamine hydrochloride.

m.p.: 103–105° C. (diisopropyl ether); $^1$H-NMR (DMSO-d$_6$, δ): 3.22 (bs, 3H), 3.85 (t, J=4.9 Hz, 2H), 4.03–4.16 (m, 4H), 4.53–4.80 (m, 4H), 5.22 (bs, 2H), 5.89 (s, 2H), 7.12–7.40 (m, 5H), 7.67 (s, 1H).

Example 8

Preparation of 2-amino-9-[2-[hexyl-( 2,2,2-trifluoroethyl) phosphonyl-methoxy]ethyl]-6-(dimethylamino)purine p-Toluenesulfonic acid (10 mg) was added to a solution of 2-amino-9-[2-[bis(2,2,2-trifluoroethyl)phosphonylmethoxy] ethyl]-6-(dimethylamino)purine (0.96 g, 2.0 mmol) in 1-hexanol (5 ml), and the mixture was stirred at 110° C. for ten hours. The reaction mixture was cooled to room temperature and concentrated to dryness. The residue was dissolved in chloroform and adsorbed on a silica gel in a column, and eluted with 1%-methanol/chloroform to obtain the title compound (771 mg, 80%).

$^1$H-NMR (CDCl$_3$, δ): 0.88 (t, J=6.6 Hz, 3H), 1.20–1.46 (m, 6H), 1.55–1.72 (m, 2H), 3.45 (s, 6H), 3.80–3.96 (m, involving d at 3.83, J=8.2 Hz, 4H), 4.00–4.16 (m, 2H), 4.18–4.46 (m, 4H), 4.61 (s, 2H), 7.54 (s, 1H).

Example 9
Preparation of 2-amino-9-[2-[bis(2,2,2-trifluoroethyl) phosphonylmethoxy]-ethyl]-6-(isopropylmethylamino) purine (Compound No. 14 in Table 1)

The title compound having the physicochemical properties set out below was obtained as oil in the same manner as in Example 2, except that isopropylmethylamine was used instead of the dimethylamine hydrochloride.

$^1$H-NMR (CDCl$_3$, δ): 1.24 (d, J=6.7 Hz, 6H), 3.21 (s, 3H), 3.88–4.02 (m, 4H), 4.17–4.50 (m, 6H), 4.57 (s, 2H), 7.51 (s, 1H).

Example 10
Preparation of 2-amino-9-[2-[bis(2,2,2-trifluoroethyl) phosphonyl-methoxy]ethyl]-6-(methylphenylamino)purine (Compound No. 621 in Table 1)

The title compound having the physicochemical properties set out below was obtained in the same manner as in Example 1, except that 2-amino-6-(methyl phenylamino) purine was used instead of the 2-amino-6-(dimethylamino) purine.

m.p.: 147–152° C. (ethyl acetate, diisopropyl ether); $^1$H-NMR (CDCl$_3$, δ): 3.78 (s, 3H), 3.86–3.96 (m, involving d at 3.91, J=7.8 Hz, 4H), 4.18–4.48 (m, 6H), 4.61 (s, 2H), 7.24–7,52 (m, 6H).

Example 11
Preparation of 2-amino-9-[2-[bis(2,2,2-trifluoroethyl) phosphonyl-methoxy]ethyl]-6-(phenylamino)purine (Compound No. 613 in Table 1)

The title compound having the physicochemical properties set out below was obtained in the same manner as in Example 1 except that 2-amino-6-(phenylamino)purine was used instead of the 2-amino-6-(dimethylamino)purine.

m.p.: 126° C. (isopropanol); $^1$H-NMR (CDCl$_3$, δ): 3.93–3.97 (m, 4H), 4.25–4.44 (m, 6H), 4.82 (s, 2H), 7.05–7,77 (m, 6H).

Example 12
Preparation of 2-amino-9-[2-[bis(2,2,2-trifluoroethyl) phosphonyl-methoxy]propyl]-6-(phenylamino)purine (Compound No. 749 in Table 1)

The title compound having the physicochemical properties set out below was obtained as syrup in the same manner as in Example 1, except that 1-chloroisopropyl chloromethyl ether and 2-amino-6-(phenylamino)purine were used instead of the 2-chloroethyl chloromethyl ether and the 2-amino-6-(dimethylamino)purine.

m.p.: Syrup; $^1$H-NMR (CDCl$_3$, δ): 1.26 (d, J=5.9 Hz, 3H), 3.76–3.88 (m, 1H), 3.90–4.10 (m, 3H), 4.16–4.24 (m, 1H), 4.30–4.46 (m, 4H), 4.79 (s, 2H), 7.07 (t, J=7.4 Hz, 1H), 7.35 (t, J=7.6 Hz, 2H), 7.52 (s, 1H), 7.60 (s, 1H), 7.75 (d, J=7.6 Hz, 2H).

TEST EXAMPLE 1
Activity for inhibiting proliferation of Hepatitis B virus (HBV)

Inhibitory activity of the compounds of the present invention against proliferation of HBV was measured by a known method (K. Ueda, et al., VIROLOGY, 169, 213–216 (1989)).

2×10$^4$ HB611 cells (recombinant human liver cancer cells producing HBV) were cultured in Dulbecco's ME medium containing 10% fetal bovine serum, streptomycin (100 μg/ml), penicillin (100 IU/ml), and Geneteicin (trade name of an antibiotic sold by Life Technologies, 0.2 mg/ml) at 37° C. The medium was changed with fresh medium on the second day and fifth day of the culture, and then changed with a medium containing a test compound at a final concentration of 10 μM or 1 μM on the 8th, 11th and 14th days of the culture. DNA of the cells were collected on the 17th day of the culture. Amounts of HBV-DNA in the cells were measured by Southern blotting method and inhibitory rates against HBV-DNA synthesis were determined. Concentrations of compounds required for 50% death of HB611 cells were determined by cell titer 96 (trademark of Promega Corp.). As references, the same test was carried out by using PMEA and its bis(pivaloyloxymethyl ester). The results are shown in Table 2 below. Compound Nos. in Table 2 correspond to those in Table 1.

TABLE 2

| Compound No. | Inhibitory ratio against HBV - DNA synthesis (%) | | 50% Cytotoxic concentration for HB611 cells (μM) |
|---|---|---|---|
| | 10 μM | 1 μM | |
| 11 | 100 | 92 | >1000 |
| 13 | 100 | | >1000 |
| 15 | | 86.7 | >1000 |
| 16 | 100 | | >1000 |
| 21 | 100 | | >1000 |
| 621 | | 68 | >1000 |
| PMEA | 83 | | 334 |
| PMEAester[1] | 90 | 63.7 | 18 |

[1]PMEA bis(pivaloyloxymethyl ester)

TEST EXAMPLE 2
Inhibitory effect on HBV proliferation in a serum of a rat orally administered with a test compound A group consisting of three rats was orally administered with a test compound at a dose of 1 g/kg or 0.3 g/kg by a single oral administration. Blood of the rats was collected one hour after the administration and serum samples were prepared.

2×10$^4$ HB611 cells were cultured in Dulbecco's ME medium containing 10% fetal bovine serum, streptomycin (100 μg/ml), penicillin (100 IU/ml) and Geneteicin (0.2 mg/ml) at 37° C. The medium was changed with fresh medium on the second day and fifth day of the culture, and then changed with a medium containing 5% of the above serum (the serum of the rat orally administered with a test compound) on the 8th, 11th and 14th days of the culture. DNA of the cells were collected on the 17th day of the culture. Amounts of HBV-DNA in the cells were measured by Southern blotting method, and inhibitory ratios against HPV-DNA synthesis in the cells were determined. As a reference, the same test was carried out by using PMEA. The results are shown in Table 3 below. Compound Nos. in Table 3 correspond to those in Table 1.

TABLE 3

| Compound No. | Dose of oral administration (g/kg) | Inhibitory ratio against HBV-DNA synthesis (%) |
|---|---|---|
| 11 | 0.3 | 95.6 |
| 13 | 0.3 | 100 |
| PMEA | 1 | 35.5 |

TEST EXAMPLE 3
Micronucleus test using mice

A test compound was administered to mice at a dose of 1,000 or 2,000 mg/kg, and bone marrow smear preparations were prepared at 24, 30, 48, and 72 hours after the administration. For a negative control group (0.5% aqueous solution of tragacanth gum) and a positive control group (2 mg/kg of mitomycin C (MMC) was administered as a single intraperitoneal administration), bone marrow smears were prepared at 24 hours after the administration. The samples were stained by the Giemsa's staining method in an ordinary manner, and then 2,000 polychromatic erythrocytes per animal were examined to determine the number of cells having micronuclei and frequency of appearance of micronuclei (%). As statistic analysis, significant difference test was carried out for polychromatic erythrocytes containing micronuclei between the negative control group and the group administered with a test compound according to the stochastic method of Kasternbaum and Bowman.

For comparison, the same test was carried out by using an unsubstituted 6-amino derivative, i.e., 9-[2-[bis(2,2,2-trifluoroethyl)phosphonylmethoxy]ethyl]-2,6-diaminopurine (abbreviated as "DAP"), and PMEA bis (pivaloyloxymethyl ester). The results are shown in Table 4 below. Compound Nos. in Table 4 correspond to those in Table 1.

TABLE 4

| Compound No. | Test result |
| --- | --- |
| 11 | Negative |
| 13 | Negative |
| DAP | Positive |
| PMEA ester[1] | Positive |

[1]PMEA bis(pivaloyloxymethyl ester)

INDUSTRIAL APPLICABILITY

The phosphonate nucleotide derivatives of the present invention have excellent antiviral activity and high oral absorbability. Therefore, they are expected to be useful as medicaments.

What is claimed is:

1. A phosphonate nucleotide derivative represented by the following general formula (I) or a salt thereof, or a hydrate or a solvate thereof:

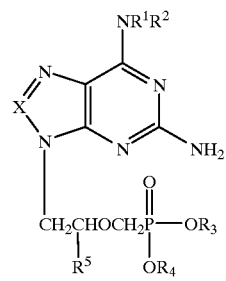

(I)

wherein $R^1$ represents hydrogen atom, a $C_1$–$C_6$ alkyl group, or a $C_7$–$C_{10}$ aralkyl group; $R^2$ represents a $C_1$–$C_6$ alkyl group, a $C_7$–$C_{10}$ aralkyl group, or phenyl group; $R^3$ and $R^4$ independently represent an ethyl group substituted with one or more halogen atoms; $R^5$ represents hydrogen atom, a $C_1$–$C_4$ alkyl group, a $C_1$–$C_4$ hydroxyalkyl group or a $C_1$–$C_4$ alkyl group substituted with one or more halogen atoms; and X represents —CH—.

2. The compound or the salt thereof, or the hydrate or the solvate thereof according to claim 1, wherein $R^1$ is hydrogen atom or a $C_1$–$C_4$ alkyl group; $R^2$ is a $C_1$–$C_4$ alkyl group, benzyl group, or phenyl group; and $R^5$ is hydrogen atom or a $C_1$–$C_4$ alkyl group.

3. The compound or the salt thereof, or the hydrate or the solvate thereof according to claim 1, wherein $R^1$ is hydrogen atom or a $C_1$–$C_4$ alkyl group; $R^2$ is a $C_1$–$C_4$ alkyl group or phenyl group; and $R^5$ is hydrogen atom or a $C_1$–$C_4$ alkyl group.

4. The compound or the salt thereof, or the hydrate or the solvate thereof according to claim 1, wherein $R^2$ is phenyl group.

5. The compound or the salt thereof, or the hydrate or the solvate thereof according to claim 1, wherein $R^1$ is hydrogen atom or a $C_1$–$C_4$ alkyl group; $R^2$ is phenyl group; and $R^5$ is hydrogen atom or a $C_1$–$C_4$ alkyl group.

6. The compound or the salt thereof, or the hydrate or the solvate thereof according to claim 1, wherein $R^5$ is a $C_1$–$C_4$ alkyl group.

7. The compound or the salt thereof, or the hydrate or the solvate thereof according to claim 1, wherein $R^1$ and $R^2$ are independently a $C_1$–$C_4$ alkyl group; and $R^5$ is a $C_1$–$C_4$ alkyl group.

8. The compound or the salt thereof, or the hydrate or the solvate thereof according to claim 1, wherein said compound is selected from the group consisting of the following compounds:

2-amino-9-[2-[bis(2,2,2-trifluoroethyl)phosphonylmethoxy]ethyl]-6-(phenylamino)purine;

2-amino-9-[2-[bis(2,2,2-trifluoroethyl)phosphonylmethoxy]ethyl]-6-(N-methylphenylamino)purine;

2-amino-9-[2-[bis(2,2,2-trifluoroethyl)phosphonylmethoxy]propyl]-6-(phenylamino)purine;

2-amino-9-[2-[bis(2,2,2-trifluoroethyl)phosphonylmethoxy]propyl]-6-(N-methylphenylamino)purine; and 2-amino-9-[2-[bis(2,2,2-trifluoroethyl)phosphonylmethoxy]propyl]-6-(dimethylamino)purine.

9. A pharmaceutical composition which comprises the compound or the salt thereof, or the hydrate or the solvate thereof according to claim 1 together with a pharmaceutically acceptable carrier.

10. A method for therapeutic treatment of a viral infectious disease which comprises the step of administering a therapeutically effective amount of the compound or the salt thereof, or the hydrate or the solvate thereof according to claim 1 to a patient with the viral disease.

11. The compound or the salt thereof, or the hydrate or the solvate thereof according to claim 2, wherein $R^2$ is phenyl group.

12. The compound or the salt thereof, or the hydrate or the solvate thereof according to claim 2, wherein $R^5$ is a $C_1$–$C_4$ alkyl group.

13. The compound or the salt thereof, or the hydrate or the solvate thereof according to claim 3, wherein $R^5$ is a $C_1$–$C_4$ alkyl group.

* * * * *